US009895466B2

(12) United States Patent
Denyer et al.

(10) Patent No.: US 9,895,466 B2
(45) Date of Patent: Feb. 20, 2018

(54) LIPOSOMAL DRUG DELIVERY SYSTEM FOR BONE CEMENTS

(71) Applicant: UNIVERSITY COLLEGE CARDIFF CONSULTANTS LIMITED, South Glamorgan (GB)

(72) Inventors: Stephen Denyer, Chepstow (GB); Samuel Evans, Cardiff (GB); Wayne Ayre, Cardiff (GB); James Birchall, Cardiff (GB)

(73) Assignee: UNIVERSITY COLLEGE CARDIFF CONSULTANTS LIMITED, Cardiff, South Glamorgan (GB)

( * ) Notice: Subject to any disclaimer, the term of this patent is extended or adjusted under 35 U.S.C. 154(b) by 0 days.

(21) Appl. No.: 14/903,803

(22) PCT Filed: Jul. 9, 2014

(86) PCT No.: PCT/GB2014/052085
§ 371 (c)(1),
(2) Date: Jan. 8, 2016

(87) PCT Pub. No.: WO2015/004450
PCT Pub. Date: Jan. 15, 2015

(65) Prior Publication Data
US 2016/0158405 A1   Jun. 9, 2016

(30) Foreign Application Priority Data

Jul. 10, 2013 (GB) .................................. 1312344.3

(51) Int. Cl.
A61K 9/00 (2006.01)
A61K 51/12 (2006.01)
A61K 9/127 (2006.01)
A61L 24/00 (2006.01)
A61L 27/54 (2006.01)
A61K 31/7036 (2006.01)
A61L 24/04 (2006.01)

(52) U.S. Cl.
CPC ........ *A61L 24/0015* (2013.01); *A61K 9/1271* (2013.01); *A61K 31/7036* (2013.01); *A61L 24/0094* (2013.01); *A61L 24/046* (2013.01); *A61L 27/54* (2013.01); *A61L 2300/23* (2013.01); *A61L 2300/406* (2013.01); *A61L 2300/626* (2013.01); *A61L 2430/02* (2013.01)

(58) Field of Classification Search
CPC . A61L 2300/626; A61K 9/0024; A61K 51/12; A61K 9/127
See application file for complete search history.

(56) References Cited

U.S. PATENT DOCUMENTS

2007/0092572 A1* 4/2007 Balaban .............. A61L 24/0015
                                                    424/487
2011/0070295 A1* 3/2011 Javeri ................... A61K 9/1278
                                                    424/450

FOREIGN PATENT DOCUMENTS

CN        101095659 A      1/2008
CN        101905033 A     12/2010
WO    WO 8904674 A1 *      6/1989    ......... A61F 2/30767

OTHER PUBLICATIONS

Wang et al. Pluronic L61 as a long-circulating modifier for enhanced liposomal delivery of cancer drugs. Mar. 27, 2013. Polymer Chemistry. vol. 4. pp. 2958-2962.*
P&T Community. Breast Cancer Drug, EndoTAG-1, Shows Promise in Phase II Trial. May 16, 2013. <http://www.pharmscope.com/news/2013-05-17-000000/breast-cancer-drug-endotag-1-shows-promise-phase-ii-trial>.*
John Hopkins Medicine. Antibiotic Slows Growth of Bladder, Breast Cancer Cells. Jan. 19, 2011. <http://www.hopkinsmedicine.org/news/media/releases/antibiotic_slows_growth_of_bladder_breast_cancer_cells>.*
Croy, Scott R., et al. The effects of Pluronic block copolymers on the aggregation state of nystatin; Journal of Controlled Release 95 (2004) 161-171; www.elsevier.com/locate/jconrel.
Kostarelos, K., et al., Physical Conjugation of (Tri-) Block Copolymers to Liposomes toward the Construction of Sterically Stabilized Vesicle Systems; Langmuir 1999, 15, 369-376.
Krylova, O.O., et al., Pluronic L61 Accelerates Flip—Flop and Transbilayer Doxorubicin Permeation; Chem. Eur. J. 2003, 9, 3930-3936. Wiley-VCH Verlag GmbH & Co. KGaA, Weinheim.
Liang, X, et al., Effect of chain lengths of PEO-PPO-PEO on small unilamellar liposome morphology and stability: an AFM investigation; Journal of Colloid and Interface Science 285 (2005) 360-372; www.elsevier.com/locate/jcis.
Roeder, B., et al., Antibiotic Beads in the Treatment of Diabetic Pedal Osteomyelitis; The Journal of Foot and Ankle Surgery, 39(2): 124-130 (2000).
Zhirnov, A. et al., Lipid composition determines interaction of liposome membranes with Pluronic L61; Biochimica et Biophysica Acta 1720 (2005) 73-83; http://www.elsevier.com/locate/bba.
Search Report dated Jan. 4, 2014 of the Patent Office of Great Britain.
CN101095659A English machine translation.
CN101905033A English machine translation.

* cited by examiner

*Primary Examiner* — Tracy Liu
(74) *Attorney, Agent, or Firm* — King & Schickli, PLLC

(57) ABSTRACT

The invention relates to a novel antibiotic delivery vehicle for impregnating bone cement wherein said vehicle is an antibiotic encapsulated liposome having a block co-polymer on its surface; a method for the manufacture of a bone cement impregnated with antibiotic or a mixture of antibiotics using said vehicle; and also a novel bone cement made therewith and/or thereby.

16 Claims, 12 Drawing Sheets

|  | Sample 1 | Sample 2 | Sample 3 |
|---|---|---|---|
| 10ug control disc | | | |
| Palacos R | | | |
| Palacos R+G | | | |
| Palacos L61 | | | |

LIPOSOMAL DRUG DELIVERY SYSTEM FOR BONE CEMENTS

This application is the national stage of international patent application no. PCT/GB2014/052085 filed on Jul. 9, 2014 which in turn claims priority from British Patent Application No. 13123443 filed on Jul. 10, 2013, the disclosures of which are incorporated herein by reference in their entirety.

TECHNICAL FIELD

The invention relates to a novel antibiotic delivery vehicle for impregnating bone cement; a method for the manufacture of a bone cement impregnated with antibiotic using said vehicle; and also a novel bone cement made therewith and/or thereby.

BACKGROUND

Replacement arthroplasty, or joint replacement surgery, is a form of orthopaedic surgery involving the musculoskeletal system wherein joint or joint surface tissue is replaced with a prosthesis, often used to treat or alleviate symptoms associated with, or caused by, musculoskeletal trauma, sports injuries, degenerative diseases, infections, tumours, and congenital disorders. One such example is the hip joint that is affected by osteoarthritis. It may be replaced entirely (total hip arthroplasty) with a prosthetic hip. The procedure involves replacing both the acetabulum (hip socket) and the head and neck of the femur. The purpose of performing this surgery is to relieve pain, to restore range of motion and to improve walking ability, leading to the improvement of muscle strength.

Joint replacement surgery, however, is often considered as a last option when the severe joint pain or dysfunction experienced by the patient is no longer alleviated by less-invasive therapies. This intervention is mainly late-stage due to the medical and intra-operative risks associated with such a major form of surgery, but also more immediate risks such as joint dislocation, loss of motion and weakness, and infection. Additionally, loosening of the prosthetic components may give rise to long term problems where the component moves inside the bone causing pain, which may also result in fragments of wear that can cause an inflammatory reaction and bone absorption (osteolysis).

In an attempt to overcome some of these issues, it is common practice to use bone cements to anchor artificial joints. The bone cement fills the free space between the prosthesis and the bone and performs the important role of an elastic zone reducing stress concentrations that may arise. A common bone cement is poly(methyl methacrylate) (PMMA), which has been used since the 1950s as a self-setting polymer to improve the fixation of prosthetic implants in orthopaedics, in particular knee and hip arthroplasty. More recently bone cement has been used in the spine in either vertebroplasty or kyphoplasty procedures. Bone cement is considered a reliable anchorage material. It is easy to use in clinical practice and has a proven long survival rate when used with cemented-in prostheses. A prosthetic fixed with bone cement offers very high primary stability combined with fast remobilization of patients. The cemented-in prosthesis can be fully loaded very soon after the operation, and the necessary rehabilitation is comparatively simple for those patients.

However, as stated, a problem that can occur as a consequence of orthopaedic surgery is bacterial colonisation, leading to infections and inflammatory responses which are known to result in the eventual failure of the implant. To overcome this problem, antibiotics can be added to the cement. The antibiotics, advantageously, are released locally after implant placement without subjecting the body in general to unnecessarily high antibiotic levels. The use of antibiotics in this way has been confirmed to reduce the danger of infection. Antibiotic cements are also advantageously used when replacing implants that have previously become infected. Temporary PMMA spacers containing antibiotics can also be employed when replacing infected implants.

When making commercially available bone cements antibiotics are mixed in a powdered form with the cement mixture. This method, although widely adopted, has several key disadvantages. For instance, when using bone cements impregnated with antibiotics, consideration must be given to the release profile of the antibiotic from the cement into the surrounding tissue; too much powdered antibiotic in the bone cement can actually be detrimental, due to weakening of the mechanical stability of the fixed prosthesis. It is also known that powdered antibiotic has a tendency to agglomerate, resulting in stress concentrations, and leaving large pores when the antibiotic is released that are detrimental to the structural integrity of the cement. Additionally, this common method of incorporation has been shown to exhibit poor release profiles, typically with high release of antibiotic shortly after implantation which then drastically and disadvantageously reduces post-surgery.

For example, typical antibiotics used in cements are the aminoglycosides, such as gentamicin sulphate, which are loaded into the cement at high concentrations (typically 0.5 g to 1 g per 40 g of PMMA bone cement). These high concentrations can lead to increased costs and also weakening of the cement, reducing its mechanical properties. Although large quantities of the antibiotic are introduced into the cement, only fractions of it are released into the surrounding tissue (0-10%) and this mostly occurs within the first 6 hours of implantation. This is caused by the diffusion of antibiotic from the surface of the cement only, leaving the bulk of the antibiotic deeper in the cement mantle.

We describe herein a novel antibiotic delivery vehicle for delivering and dispersing antibiotic in bone cement such that the resultant product exhibits uniform mixing of antibiotic in the cement thus having an improved antibiotic release profile and surprising structural advantages without compromising the mechanical strength and/or fatigue properties of the cement.

SUMMARY

According to a first aspect of the invention there is provided a vehicle for delivering and dispersing at least one antibiotic in bone cement comprising a liposome containing said antibiotic wherein said liposome comprises a block co-polymers having an average molecular weight less than 2000 and a higher proportion of polypropylene oxide to polyethylene oxide.

Reference herein to the term block co-polymers is reference to a nonionic triblock copolymer composed of a central hydrophobic chain of polyoxypropylene (poly(propylene oxide) flanked by hydrophilic chains of polyoxyethylene (poly(ethylene oxide). Block co-polymers are also known under the trade names of Pluronics, Poloxamers, Synperonics and Kolliphors.

Naming of the Pluronics described herein follows convention in that these copolymers start with a letter to define their physical form at room temperature (L=liquid, P=paste, F=flake (solid)) followed by two or three digits. The first digit (two digits in a three-digit number) in the numerical designation, multiplied by 300, indicates the approximate molecular weight of the hydrophobe; and the last digit×10 gives the percentage polyoxyethylene content (e.g., L61=Pluronic with a polyoxypropylene molecular mass of 1,800 g/mol and a 10% polyoxyethylene content).

Notably, naming of other block co-polymers that can be used to exemplify the invention is similar but not identical to the above. For example Poloxamers are the same as Pluronics, just a different name/label. Poloxamers are commonly named with the letter "P" (for poloxamer) followed by three digits, the first two digits×100 give the approximate molecular mass of the polyoxypropylene core, and the last digit×10 gives the percentage polyoxyethylene content (e.g., P407=Poloxamer with a polyoxypropylene molecular mass of 4,000 g/mol and a 70% polyoxyethylene content. This Poloxamer is the same as Pluronic F127).

Those skilled in the art will appreciate that block co-polymers, whether termed Pluronics, Poloxamers, Synperonics and Kolliphors may be used to work the invention provided they have the inventive features described herein.

In a preferred embodiment of the invention said liposome is less than 600 nm in diameter when measured using laser diffraction or, alternatively, said liposome is less than 150 nm in diameter when measured using Transmission Electron Microscopy TEM. Preferably said liposomes are most favourably 100 nm when measured using Transmission Electron Microscopy TEM, ideally in methyl methacrylate Moreover said liposomes are made from at least one phospholipid selected from at least one of the following groups: phospatidylcholine, phosphatidylethanolamine, sphingomyelin, phosphatidic acid, phospatidylglycerol, phospatidylserine and phospatidylinositol. Alternatively, or additionally, said liposomes are made from at least one cationic (positively charged) lipid selected from at least one of the following groups 1,2 dioleoyl-3-trimethylammoniumpropane DOTAP, dioctadecyldimethylammonium chloride DODAc, 1,2-dimyristoyloxypropyl-3-dimethyl-hydroxyethyl ammonium DMRIE, 2,3-dioleoyloxy-N-(2(sperminecarboxamide)ethyl)-N,N-dimethyl-1 propananninium DOSPA, dioctadecylamidoglycylspermine DOGS, 1,2-dimethyl-dioctadecylammoniumbromide DDAB, 2-dioleyl-3-N,N,N-trimethylaminopropanechloride DOTMA, 1,2-dimyristoyl-3-trimethylammoniumpropane DMTAP, 1,2-distearoyl-3-trimethylammoniumpropane DSTAP, 1,2-Dioleoyl-3-dimethylammonium-propane DODAP, 1,2-dioleoyl-sn-glycero-3-phosphoethanolamine DOPE and N-(4-carboxybenzyl)-N,N-dimethyl-2,3-bis(oleoyloxy)propan-1-aminium DOBAQ.

The structures of the candidate lipids for the manufacture of liposomes are shown in FIG. 16. Those skilled in the art will appreciate that, ideally but not exclusively, lipids with the same charge as the materials to be encapsulated tend to be incompatible as the charges repel one another due to electrostatic interactions. It therefore follows that the liposome lipid will be selected having regard to the nature of the antibiotic to be encapsulated. Thus negatively charged antibiotic is typically, but not exclusively, best encapsulated in a liposome that is predominantly made of positively charged lipids such as DOTAP, DODAc, DMRIE, DOSPA, DMTAP, DSTAP, DODAP, DOBAQ, DDAB or DOGS; or alternatively a liposome that is predominantly made of neutrally charged lipids such as phospatidylcholine, phosphatidylethanolamine or sphingomyelin.

Reference herein to a liposome predominantly made of a specified charge is reference to a liposome having a greater amount of lipid or lipids with the desired charge compared to the amount of lipid or lipids with another charge, where reference to charge includes positive, negative or neutral.

Alternatively, in some embodiments, the liposomes will comprise either cationic, neutral or anionic phospholipids or one or more combinations thereof.

Also, reference herein to a liposome containing at least one antibiotic includes reference to an antibiotic contained in either the lipophilic region of the liposome or the aqueous compartment. For example a non-polar antibiotic may be incorporated into the lipophilic region of the liposome rather than the aqueous compartment.

Table 3 shows the liposomal-based therapeutics that have been clinically approved and Table 4 shows the liposome-based therapeutics currently undergoing clinical trials. Both tables show the liposome composition for each product; the overall charge of the liposomal system; the therapeutic agent encapsulated and the approved indication. Any one or more of these liposomes may be used in the working of the invention and the nature of the selected liposome will be chosen having regard to the overall liposome charge and the charge of the antibiotic to be encapsulated.

More preferably said antibiotic is selected from the list comprising gentamicin, vancomycin, tobramycin, ampicillin, benzylpenicillin, erythromycin, kanamycin, methicillin, neomycin, streptomycin, tetracycline, co-trimoxazole, cloxacillin, chloramphenicol, cephaloridine, cephazolin, oxacillin, ciprofloxacin, aztreonam and imipenem. This list is supplied for the purpose of illustrating the working of the invention, other antibiotics may be used in the working of the invention and are known to those skilled in the art. Moreover, combinations of antibiotics may be used, selected on the basis of their synergistic effect or suitability for the nature of the infection or potential infection to be treated, for example:

Oxacillin+kanamycin or amikacin against *S. aureus*;
Ampicillin+gentamicin against *S. aureus*;
Cephazolin+vancomycin and imipenem+vancomycin against MRSA;
Aztreonam+ciprofloxacin against *P. aeruginosa* biofilms; and
more generally, beta-lactam agents combined with aminoglycosides.

Additionally or alternatively, said at least one antibiotic comprises, in addition to said antibiotic, other antimicrobial agents, or drugs to stimulate bone formation or selected therapeutic agents such as, without limitation, strontium, bisphosphonates or bone morphogenic proteins.

We show herein that by adsorbing amphiphilic block copolymers (Pluronics) on the surface of liposomes (FIG. 2), one can change the surface properties of the liposomes which, advantageously, permits uniform mixing of these liposomes, ideally antibiotic-loaded liposomes, into a polymer such as bone cement. Moreover, once this process is undertaken the resultant product, or bone cement, shows a greatly improved antibiotic release profile compared to conventional products. Further, surprisingly we have also found that bone cements made in this way have unexpected structural advantages without compromising the mechanical strength and/or fatigue properties of the polymer.

Reference herein to uniform mixing of the liposomes in a polymer is reference to their ability to remain dispersed, or suspended, in a fluid (hydrophobic or hydrophilic) of said polymer or a precursor thereof; in other words to create stable suspensions as illustrated in FIG. 7.

Accordingly in a further aspect the invention concerns a bone cement in which there is dispersed a plurality of vehicles for delivering and dispersing at least one antibiotic within said cement wherein said vehicles comprise liposomes containing said antibiotic and further wherein said liposomes comprise a block co-polymers having an average molecular weight less than 2000 and a higher proportion of polypropylene oxide to polyethylene oxide.

In yet a further preferred embodiment of the invention said cement is selected from the group comprising: poly (methyl methacrylate) (PMMA), methacrylate-based cements or acrylic resins.

In a preferred embodiment of the invention said liposome is less than 600 nm in diameter when measured using laser diffraction or, alternatively, said liposome is less than 150 nm in diameter when measured using Transmission Electron Microscopy TEM.

In yet a further preferred embodiment of the invention said cement comprises a plurality of said liposomes. Preferably said liposomes are most favourably 100 nm when measured using Transmission Electron Microscopy TEM, ideally in methyl methacrylate.

Moreover said liposomes are made from at least one phospholipid selected from at least one of the following groups phospatidylcholine, phosphatidylethanolamine, sphingomyelin, phosphatidic acid, phospatidylglycerol, phospatidylserine and phospatidylinositol. Alternatively, or additionally, said liposomes are made from at least one cationic (positively charged) lipid selected from at least one of the following groups 1,2 dioleoyl-3-trimethylammonium-propane DOTAP, dioctadecyldimethylammonium chloride DODAc, 1,2-dimyristoyloxypropyl-3-dimethyl-hydroxy-ethyl ammonium DMRIE, 2,3-dioleoyloxy-N-(2(spermin-ecarboxamide)ethyl)-N,N-dimethyl-1 propananninium DOSPA, dioctadecylamidoglycylspermine DOGS, 1,2-dimethyl-dioctadecylammoniumbromide DDAB, 2-dioleyl-3-N,N,N-trimethylaminopropanechloride DOTMA, 1,2-dimyristoyl-3-trimethylammoniumpropane DMTAP, 1,2-distearoyl-3-trimethylammoniumpropane DSTAP, 1,2-Dioleoyl-3-dimethylammonium-propane DODAP, 1,2-dioleoyl-sn-glycero-3-phosphoethanolamine DOPE and N-(4-carboxybenzyl)-N,N-dimethyl-2,3-bis(oleoyloxy)pro-pan-1-aminium DOBAQ.

In a preferred embodiment of the invention the liposomes' lipid ideally, but not exclusively, is selected having regard to the nature of the antibiotic to be encapsulated. Thus, typically, but not exclusively, the charge of the antibiotic will determine the predominance of the opposite, or neutral, charge of the lipid liposomes.

In yet a preferred embodiment of the invention said plurality of lipid liposomes comprises one or more types of liposomes thus, in one embodiment, mixtures of liposomes of differing compositions are used, typically but not exclusively, in order to carry and deliver different types of antibiotics from the cement. For example, in different embodiments said plurality of liposomes is selected from one or more of the groups comprising: liposomes made from the same lipid; liposomes made from the same two or more different types of lipids; different liposomes made from a different type of lipid; different liposomes made from different two or more types of lipids; liposomes made from the same one or more types of lipid(s) but containing different antibiotics; and liposomes made from different one or more types of lipids but containing different antibiotics.

Reference herein to a liposome predominantly made of a specified charge is reference to a liposome having a greater amount of lipid or lipids with the desired charge compared to the amount of lipid or lipids with another charge, where reference to charge includes positive, negative or neutral.

Alternatively, in some embodiments, the liposomes will comprise either cationic, neutral or anionic phospholipids or one or more combinations thereof.

Also, reference herein to a liposome containing at least one antibiotic includes reference to an antibiotic contained in either the lipophilic region of the liposome or the aqueous compartment. For example a non-polar antibiotic may be incorporated into the lipophilic region of the liposome rather than the aqueous compartment In yet a further preferred embodiment of the invention said liposomes are made from any one or more of the liposomes shown in Table 3 or 4.

More preferably said antibiotic is selected from the list comprising gentamicin, vancomycin, tobramycin, ampicillin, benzylpenicillin, erythromycin, kanamycin, methicillin, neomycin, streptomycin, tetracycline, co-trimoxazole, cloxacillin, chloramphenicol, cephaloridine, cephazolin, oxacillin, ciprofloxacin, aztreonam and imipenem. This list is supplied for the purpose of illustrating the working of the invention, other antibiotics may be used in the working of the invention and are known to those skilled in the art.

More preferably still said at least one antibiotic comprises a combination of antibiotics selected on the basis of their synergistic effect or suitability for the nature of the infection or potential infection to be treated, for example:

Oxacillin+kanamycin or amikacin against *S. aureus;*
Ampicillin+gentamicin against *S. aureus;*
Cephazolin+vancomycin and imipenem+vancomycin against MRSA;
Aztreonam+ciprofloxacin against *P. aeruginosa* biofilms; and
more generally, beta-lactam agents combined with aminoglycosides.

Additionally or alternatively, said at least one antibiotic comprises, in addition to said antibiotic, other antimicrobial agents, or drugs to stimulate bone formation or selected therapeutic agents such as, without limitation, strontium, bisphosphonates or bone morphogenic proteins.

According to a further aspect of the invention there is provided a method for the manufacture of bone cement comprising mixing together a polymer suitable for making bone cement, or a precursor thereof, with a plurality of vehicles according to the invention. This method thus provides for at least one antibiotic contained within said vehicle to be delivered and dispersed in said bone cement.

Reference herein to a precursor thereof includes reference to the monomeric components of the polymer or indeed any other precursor of the polymer that is suitable for making bone cement.

In a preferred method of the invention a liposomal suspension of said vehicles is mixed into the liquid component of the bone cement prior to mixing this liquid component with the non-liquid component of the bone cement.

This method provides a better overall dispersion of the antibiotic in the cement compared to conventional techniques which tend to agglomerate antibiotic powder particles, thereby preventing uniform and controlled release of the antibiotic from the bulk of the cement.

Throughout the description and claims of this specification, the words "comprise" and "contain" and variations of the words, for example "comprising" and "comprises", mean "including but not limited to" and do not exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

All references, including any patent or patent application, cited in this specification are hereby incorporated by reference. No admission is made that any reference constitutes prior art. Further, no admission is made that any of the prior art constitutes part of the common general knowledge in the art.

Preferred features of each aspect of the invention may be as described in connection with any of the other aspects.

Other features of the present invention will become apparent from the following examples. Generally speaking, the invention extends to any novel one, or any novel combination, of the features disclosed in this specification (including the accompanying claims and drawings). Thus, features, integers, characteristics, compounds or chemical moieties described in conjunction with a particular aspect, embodiment or example of the invention are to be understood to be applicable to any other aspect, embodiment or example described herein, unless incompatible therewith.

Moreover, unless stated otherwise, any feature disclosed herein may be replaced by an alternative feature serving the same or a similar purpose.

The Invention will now be described by way of example only with reference to the Examples below and to the following Figures wherein:

BRIEF DESCRIPTION OF THE DRAWINGS

FIG. 10. Shows zones of *S. aureus* growth inhibition on agar plates for Palacos R and Palacos R+G bone cement and Palacos R cement containing gentamicin-loaded liposomes coated with Pluronic L61;

FIG. 11b. Shows SEM images of Palacos R+G and Palacos R containing liposomes coated with Pluronics L31, L43 and L61 cement samples before and after 1440 hours in Ringer's solution;

Figure 1:
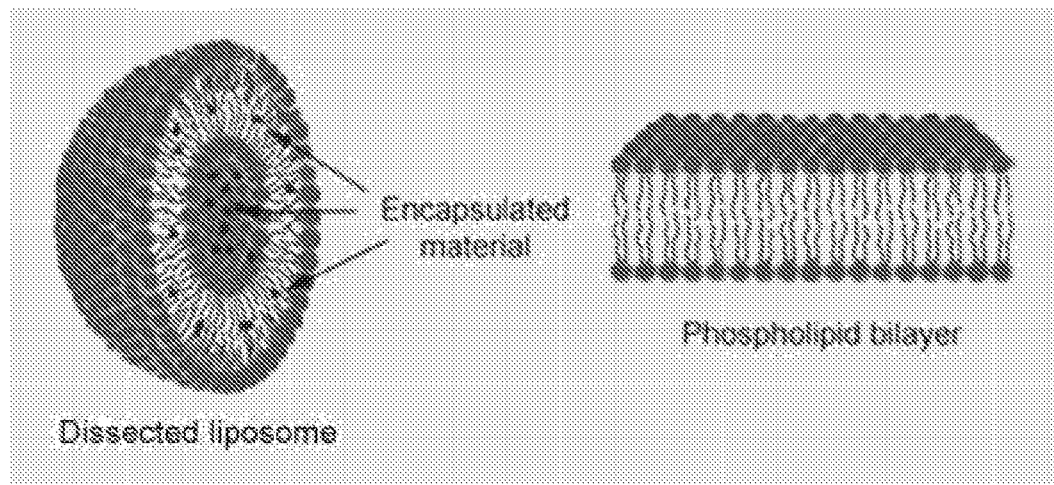
FIG. 1. Shows the structure of a liposome.
Figure 2:
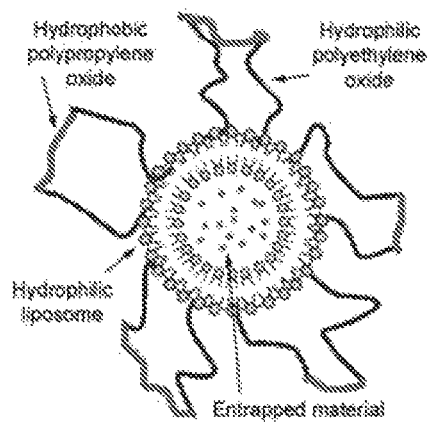
FIG. 2. Shows a diagrammatic arrangement of Pluronics on the surface of a liposome.
Figure 3:
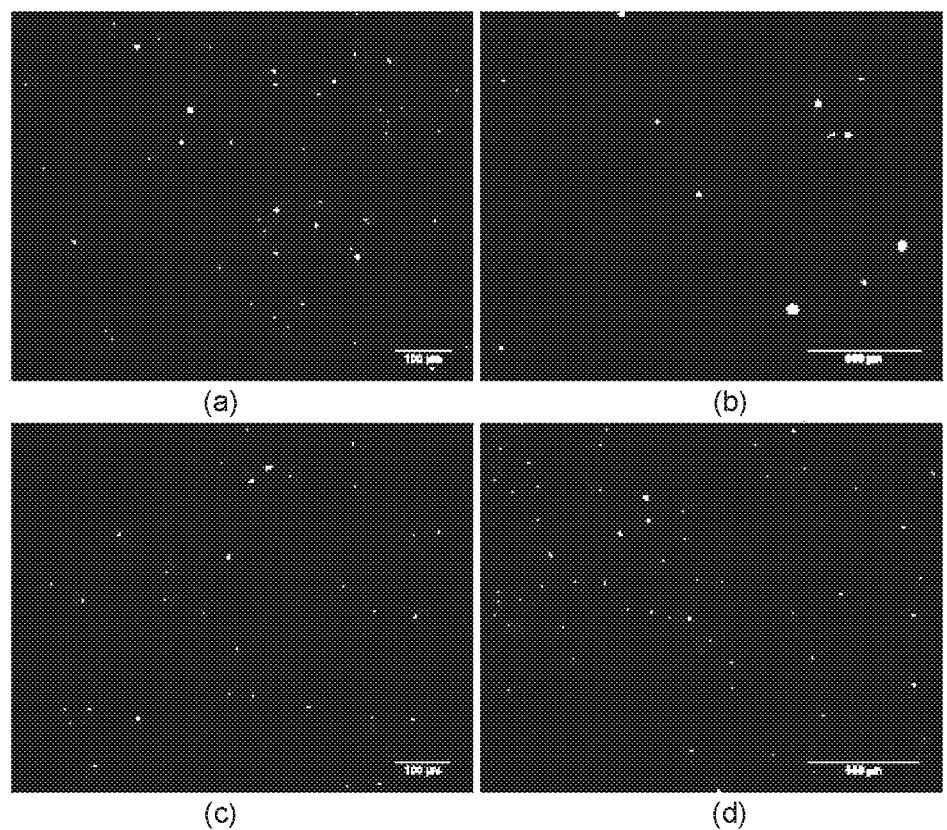
FIG. 3. Shows fluorescence microscopy images of liposomes in (a-b) water and (c-d) Palacos R, with L61 Pluronic.

Table 1. Particle sizes of Pluronic-coated liposomes in methyl methacrylate measured by laser diffraction;

Table 2. Pluronics and their properties (tested Pluronics underlined);

Table 3. Shows the liposomal-based therapeutics that have been clinically approved; and Table 4. Shows the liposome-based therapeutics currently undergoing clinical trials. Both tables show the liposome composition for each product; the overall charge of the liposomal system; the therapeutic agent encapsulated and the approved indication.

LIST OF ABBREVIATIONS

DDAB, 1,2-dimethyl-ioctadecylammoniumbromide
DMPC, 1-α-dimyristoylphosphatidylcholine
DMPG, 1-α-dimyristoylphosphatidylglycerol
DMRIE, (1,2-dimyristoyloxypropyl-3-dimethyl-hydroxyethyl ammonium)
DMTAP, 1,2-dimyristoyl-3-trimethylammoniumpropane DOBAQ, N-(4-carboxybenzyl)-N,N-dimethyl-2,3-bis(oleoyloxy)propan-1-aminium DOGS, (dioctadecylamidoglycylspermine).

DOPC, 1,2-Dioleoyl-sn-glycero-3-phosphocholine

DODAc, (dioctadecyldimethylammonium chloride)

DOTAP, 1,2 dioleoyl-3-trimethylammoniumpropane

DODAP, 1,2-Dioleoyl-3-dimethylammonium-propane

DOTMA, 2-dioleyl-3-N,N,N-trimethylaminopropan-echloride

DOPC, dioleoylphosphatidylcholine

DOPE, dioleoylphosphatidylethanolamine

DOSPA, (2,3-dioleoyloxy-N-(2(sperminecarboxamide)ethyl)-N,N-dimethyl-1 propananninium)

DPPC, dipalmitoylphosphatidylcholine

DPPG, dipalmitoylphosphatidylglycerol

DSPC, distearoylphosphatidylcholine

DSPE, distearoylphosphatidylethanolamine

DSPG, distearoylphosphatidylglycerol

DSTAP, 1,2-distearoyl-3-trimethylammoniumpropane

EPC, egg phosphatidylcholine

EPG, egg phosphatidylglycerol

HSPG, hydrogenated soy phosphatidylcholine mPEG 2000-DSPE, methoxy-polyethylene glycol-distearoyl phosphatidylethanolamine MSPC, monostearoylphosphatidylcholine PEG 2000-DSPE, polyethylene glycol 2000-distearoyl-phosphatidylethanolamine SPC, soy phosphatidylcholine

DETAILED DESCRIPTION

Materials and Methods

Preparation of Pluronic-Coated Liposomes

Phosphatidyl choline (PC) from egg yolk (≥99.0%), cholesterol (C, ≥99.0%), uranyl acetate (≥98.0%), gentamicin sulphate (≥590 ug gentamicin base per mg), o-phthaldialdehyde (≥97%, HPLC), ethanol (≥99.8%, HPLC), 2-mercaptoethanol (≥99.0%), sodium borate (≥99.0%), methyl methacrylate (MMA, 99%) and Pluronics L31, L61, F68 and F127 were purchased from Sigma Aldrich (Gillingham, UK). Chloroform (HPLC grade) was purchased from Fisher Scientific (Fisher Scientific UK Ltd, Loughborough, UK). Pluronics L43, L44, L62, L64, P65, P84, P104, P123 were provided by BASF (BASF Corporation, Connecticut, USA). TopFluor cholesterol was purchased from INstruchemie (INstruchemie BV, Delfzijl, Netherlands). Cemex and Cemex Genta were obtained from Tecres (Sommacampagna, Italy), Palacos R and Palacos R+G were provided by Heraeus (Newbury, UK) and CMW Smartset GHV was provided by Depuy (Depuy CMW, Blackpool, UK).

Phosphatidylcholine (PC) and cholesterol (C) were weighed and combined in a w/w ratio of 7:1 respectively and added to a 50 mL round-bottom flask. 5 mL of chloroform was added to the flask and the suspension was vortex mixed until the lipids dissolved. The flask was attached to a rotary evaporator with a water bath set at 60° C. (above the phase transition temperature of PC) with a vacuum pump and rotation set to 1 revolution per second. Once all the chloroform had evaporated and a thin film of lipids had formed, deionised water heated to 60° C. (above the phase transition temperature of the lipid) was added and the flask vortex mixed to create a suspension of liposome vesicles at a concentration of 5 mg/mL. The lipid suspension was held at 60° C. for 30 minutes for the liposomes to form. The suspension was extruded 10 times under nitrogen pressure (8 bars maximum) using a Lipex extruder (Northern Lipids Inc., British Columbia, Canada) through a 400 nm polycarbonate membrane (Whatman, UK) followed by further extrusion 10 times using a 100 nm polycarbonate membrane.

The average liposome diameter was measured by laser diffraction using a Beckman Coulter N4 PLUS particle size analyzer (Beckman Coulter Ltd, High Wycombe, UK) to ensure an average 100 nm diameter liposome suspension was obtained. 2% w/w of Pluronic (L31, L43, L44, L61, L62, L64, P65, F68, P84, P104, P123 or F127) was added to the liposome suspension after extrusion. The liposome-Pluronic suspension was centrifuged at 100,000 g (25,000 RPM) for 1 hour at 4° C. using a Beckman Optima LE-80K centrifuge (Beckman Coulter Ltd., High Wycombe, UK) with a SW28 rotor to create a pellet in order to minimize the amount of water in the final cement mixture.

Laser Diffraction 10 mg PC:C liposome pellets with and without the Pluronics stated above were prepared as described and resuspended in 10 mL of methyl methacrylate (MMA) by the process of titruration (progressive aliquot mixing in a mortar and pestle i.e. a small amount of MMA added to the liposome pellet to create a paste, gradually adding more MMA to produce a homogeneous mixture) using a glass mortar and pestle, followed by vortex mixing. The liposome diameters in MMA were measured by laser diffraction using a Beckman Coulter N4 PLUS particle size analyzer (Beckman Coulter Ltd, High Wycombe, UK).

Sedimentation Rate

The sedimentation rate was established by measuring the absorption of incident light at 420 nm by the liposome-Pluronic suspension in MMA over time using a Hitachi U-1900 spectrophotometer (Hitachi High-Technologies Europe GmbH, Mannheim, Germany) against an MMA blank. The suspensions were agitated initially and placed in the spectrophotometer, where the suspension was allowed to stand undisturbed over a period of one hour whilst absorption readings were taken.

Transmission Electron Microscopy

Transmission electron microscopy (TEM) was used to assess the dispersion of liposomes in MMA and water. PC:C liposomes and PC:C liposomes with L61 Pluronic were prepared as described and mixed with 4% w/v aqueous uranyl acetate in a ratio of 1:1 and left for 60 minutes. Ratio relates to the ratio of uranyl acetate added to the liposome suspension (e.g. 1 mL of liposome suspension and 1 mL of 4% w/v uranyl acetate).

The liposomes were then pelleted as described. The pellets were resuspended in water or MMA. A 10 uL droplet of each suspension was added to a Formvar carbon film on a 400 mesh Nickel grid (EM Systems Support Ltd., Macclesfield, UK) and allowed to dry in air. MMA alone was also dried on a grid as a control. The grids were observed using a Philips CM12 TEM (Philips Research, Eindhoven, Netherlands) operating at 80 kV. Images were recorded using an SIS MegaView III digital camera (Olympus Soft Imaging Solutions GmbH, Munster, Germany).

Fluorescence Microscopy

To assess the dispersion of the liposomes in a commercial cement, 100 mg of liposomal material was suspended in water at a concentration of 5 mg/mL, as described. TopFluor Cholesterol (FC, 23-(dipyrromethaneboron difluoride)-24-norcholesterol, INstruchemie BV, Delfzijl, Netherlands) was used to substitute for a portion of the cholesterol component to give a ratio of 7:0.9:0.1 of PC:C:FC. The fluorescent liposome suspension was sized using laser diffraction to ensure 100 nm liposomes were formed. 1 mL of the suspension was diluted in 4 mL of distilled deionised water to obtain a concentration of 1 mg/mL and fluorescent images were taken for observation. The remaining 5 mg/mL liposomal suspension was divided into four aliquots of 4 mL. 2% w/w of Pluronic L31, L43 or L61 was added to three of the aliquots and the suspension was pelleted as previously described. Similarly, the remaining 4 mL aliquot of 5 mg/mL liposomal suspension alone was pelleted. The four pellets were individually resuspended in 2 mL of the liquid component of Palacos R (MMA) which contains N,N-dimethyl-p-toluidine (DMPT, the initiator for the polymerisation reaction) and colorant E141 for better visibility, however it mainly consists of the same MMA as above.

This was mixed with 4 g of the Palacos R powder according to the manufacturer's instructions. The cement was compressed between two glass slides to create a thin sample capable of transmitting light. All cement samples were inspected under a light microscope for pores and transparency and stored in the dark until observed using an Olympus IX50 fluorescent microscope. A green filter (495-570 nm) was used to excite the fluorescent lipids and images of the emitted red fluorescence were taken.

Liposome-Pluronic Preparation with Antibiotic

A similar method for liposome preparation was undertaken as previously outlined. 175 mg of PC and 25 mg C were weighed and added to a 50 mL round-bottom flask. 5 mL of chloroform was added to the flask and the suspension was vortex mixed until the lipids dissolved.

The flask was attached to a rotary evaporator with a water bath set at 60° C. with a vacuum pump and rotation set to 1 revolution per second. Once the chloroform had evaporated and a thin film of lipids had formed, 40 mL of 5 mg/mL gentamicin sulphate solution, heated to 60° C., was added and the flask vortex mixed to create a suspension of liposome vesicles at a concentration of 5 mg/mL. The liposome suspension was held at 60° C. for 30 minutes for the liposomes to form. The suspension was extruded 10 times under nitrogen pressure (8 bars maximum) using a Lipex extruder (Northern Lipids Inc., British Columbia, Canada) through a 400 nm polycarbonate membrane (Whatman, UK) followed by further extrusion 10 times using a 100 nm polycarbonate membrane. A Beckman Coulter N4 PLUS particle size analyzer was used to ensure an average 100 nm liposome diameter was obtained. 2% w/w of L31 Pluronics was added and the solution was centrifuged at 100,000 g (25,000 RPM) for 1 hour at 4° C. using a Beckman Optima LE-80K centrifuge with a SW28 rotor to create a pellet. The 200 mg pellet was resuspended in 20 mL of the liquid component of Palacos R (MMA) by the process of trituration, using a glass mortar and pestle, followed by vortex mixing. The method was repeated for L43 and L61 Pluronics.

Antibiotic Release

Commercially available antibiotic-loaded cements (Cemex Genta, Palacos R+G and CMW Smartset GHV) were prepared according to the manufacturer's instructions. Standard Cemex and Palacos R bone cement samples were prepared and tested to ensure leaching components of the cement did not affect measurement of antibiotic release. A 200 mg liposomal gentamicin sulphate pellet (with Pluronics L31, L43 or L61) was prepared as described and mixed with 20 mL of the MAA-based liquid component of Palacos R Cement. This was mixed with 40 g of Palacos R cement according to the manufacturer's instructions.

A high-density PTFE mould was manufactured to produce 10 mm diameter by 2 mm thick cylindrical samples. All samples were finished with a 250 grit silicon carbide sandpaper to the stated dimensions with a tolerance of ±0.2 mm. Each sample weighed 0.40±0.01 g and five samples for each test group were examined. Each sample was stored in 5 mL of Ringer's solution (8.6 mg/mL NaCl, 0.3 mg/mL KCl and 0.33 mg/mL $CaCl_2$, buffered to a pH of 7.4 with $NaHCO_3$ [1]) at 37° C. After 6 hours, 1, 2, 3, 7, 15, 30 and 60 days the Ringer's solution was removed and stored in the dark at −20° C. before assaying; 5 mL of fresh Ringer's was added as replacement until the next time point.

The solutions were thawed overnight at room temperature in the dark and the concentration of gentamicin was determined using an o-phthaldialdehyde (PHT) method developed by Sampath et al. (1990) [2] and Zhang et al. (1994) [3], whereby a PHT reagent reacts with the amino groups of gentamicin sulphate to yield measurable fluorogenic products. The reagent was prepared by adding 2.5 g of o-phthaldialdehyde, 62.5 mL of ethanol and 3 mL of 2-mercaptoethanol to 560 mL of 0.04M sodium borate solution in distilled water. The PHT reagent was stored in an amber glass bottle in the dark for 24 hours prior to use.

Twelve calibration solutions with gentamicin concentrations from 0 μg/mL to 100 μg/mL in Ringer's solution were prepared for the calibration curve. 1 mL of the calibration solution was added to 1 mL PHT reagent and 1 mL isopropanol and left for 40 minutes to react. The absorbance was then measured at 340 nm using a Hitachi U-1900 spectrophotometer (Hitachi High-Technologies Europe GmbH, Mannheim, Germany) and a linear relationship between concentration and absorbance was produced. 1 mL of the sample eluate was mixed with 1 mL PHT reagent and 1 mL isopropanol and left for 40 minutes to react and its absorbance compared against the calibration graph, in order to determine the concentration of gentamicin sulphate released by the samples at each time point. Average gentamicin concentrations for each time point were calculated from the 5 samples and the cumulative gentamicin release was calculated as a percentage of the theoretical maximum amount of gentamicin sulphate in each sample over 60 days.

Scanning Electron Microscopy

Scanning electron microscopy (SEM) images of the surfaces following release of the antibiotic into Ringer's solution for 60 days were compared with fresh samples. Prior to imaging with an EBT1 Scanning Electron Microscope (SEM Tech Ltd, Southampton, UK) at 15 KeV, the samples were gold coated using an E65x sputter coater (Emitech, Kent, UK).

Microbial Growth and Zones of Inhibition 10 mm diameter by 2 mm thick cylindrical bone cement samples were prepared as previously described for Palacos R, Palacos R+G and Palacos R with 200 mg of L61 liposomal gentamicin sulphate. Tryptone soya agar (TSA) was prepared by dissolving 40 g of tryptone soy agar medium in one liter of distilled water. The solution was boiled for one minute then sterilized in an autoclave at 121° C. for 15 minutes. The solution was allowed to cool to 45-50° C. before being dispensed into petri dishes (9 cm diameter). The petri dishes were cooled to room temperature then stored at 8-15° C. until use. *Staphylococcus aureus* (*S. aureus*) was cultured in tryptic soy broth (TSB) for 18-24 hours at 37° C. A sterile cotton swab was used to spread the inoculum across the TSA petri dish. The petri dish was turned by 60° and the process was repeated to ensure complete surface coverage. A 10 ug gentamicin standard disc was placed on the petri dish as a control and pressure was applied to the top of the disc to ensure full surface contact. The dish was divided into segments and the bone cement samples were placed well separated on the agar, in the same manner. The petri dish was then incubated at 37° C. for 18-24 hours, after which, the zones of inhibition around the samples and gentamicin disc were measured. Images of the zones of inhibition were taken and measured using ImageJ software (National Institutes of Health, Maryland, USA). The zones of inhibition were measured as the radius of the zone minus the radius of the sample. Two measurements for each zone of inhibition were taken, perpendicular to one another. The experiment was repeated in triplicate (n=3). Observations on the appearance of the bacterial cultures and the zones of inhibition were also made.

Compressive Strength

Compressive strength was determined as specified in the ISO 5833:2002 standard.[4] Cylindrical bone cement samples of Palacos R, Palacos R+G and Palacos R with 200 mg of liposomal gentamicin (with L31, L43 or L61 Pluronic) were prepared with 12±0.1 mm length and 6±0.1 mm diameter. Prior to loading, the dimensions of the samples were recorded to an accuracy of ±0.01 mm. Each individual sample was then loaded incrementally in compression using a Zwick Roell ProLine table-top Z050/Z100 materials testing machine (Zwick Testing Machines Ltd., Herefordshire, UK) at a constant cross-head speed of 20 mm/min. Load and displacement was recorded and loading was stopped when failure occurred or the upper yield point had been passed. Five samples per group were tested and the compressive strength was calculated according to the ISO 5833 standard.

Bending Strength and Modulus

Bending modulus and strength was determined as specified in the ISO 5833:2002 standard.[4] Rectangular bone cement samples were prepared for Palacos R, Palacos R+G and Palacos R with 200 mg of liposomal gentamicin (with L31, L43 or L61 Pluronic) with a length of 75±0.1 mm, width of 10±0.1 mm and thickness of 3.3±0.1 mm. Prior to loading, the width and thickness of the samples were recorded to an accuracy of ±0.01 mm. A four-point bending test rig was used with a distance between the outer loading points of 60±1 mm and a distance between the inner loading points of 20±1 mm. Each individual sample was carefully placed in the centre of the four-point bending rig and loaded incrementally using a Zwick Roell ProLine table-top Z050/Z100 materials testing machine at a constant cross-head speed of 5 mm/min. Displacement as a function of applied force was recorded. Loading was stopped when failure of the specimen occurred. Five samples per group were tested and the average bending strength and average bending modulus were calculated as described in the ISO 5833 standard.

Fracture Toughness

The ISO 13586:2000 standard was used to determine the fracture toughness of Palacos R, Palacos R+G and Palacos R with 200 mg of liposomal gentamicin (with L31, L43 or L61 Pluronic) samples.[5] This was similar to the bending tests but with a sharp chevron notch (roughly 4.5-5.5 mm) through the centre of the sample, created using a sharp razor blade. Prior to loading in three-point bending at 10 mm/min using a Zwick Roell ProLine table-top Z050/Z100 materials testing machine, a travelling (multi-axis) microscope was used to measure the length of the crack and the width and length of each sample was measured using a vernier caliper. The results from five samples for each group were recorded to obtain an average and the critical stress intensity was calculated as specified by the ISO 13586 standard.

RESULTS

Figure 4:
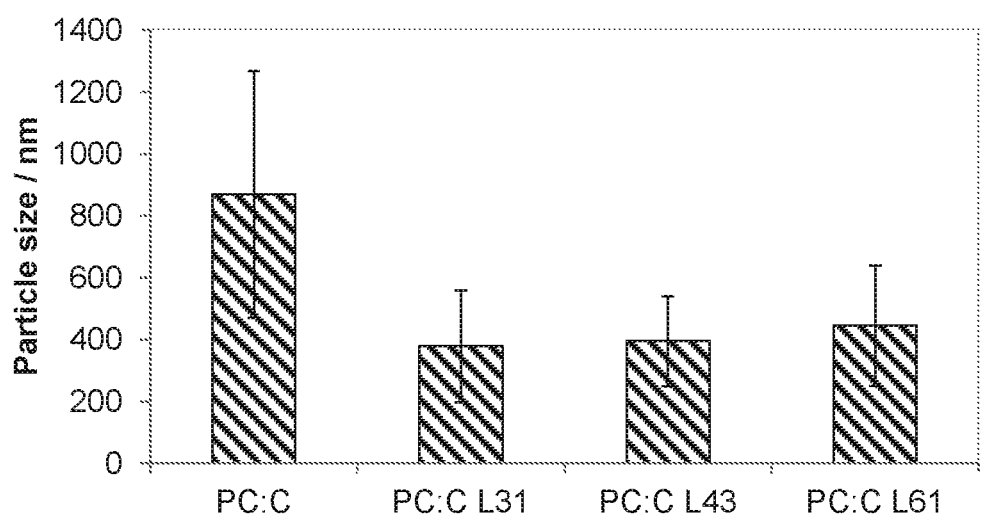
FIG. 4. Shows particle sizes of the most effective Pluronic-coated liposomes in methyl methacrylate obtained by laser diffraction.

Pluronic-Coated Liposomes Exhibit Different Particle Size in Methyl Methacrylate Using Laser Diffraction Table 1 shows the particle sizes of the liposomes in methyl methacrylate measured by laser diffraction. L31, L43 and L61 Pluronic gave significantly smaller particle sizes when compared to the other Pluronics. FIG. 4 shows nascent liposomes suspended in methyl methacrylate and the Pluronic coated liposomes that gave particle sizes below 600 nm using laser diffraction.

Figure 5:
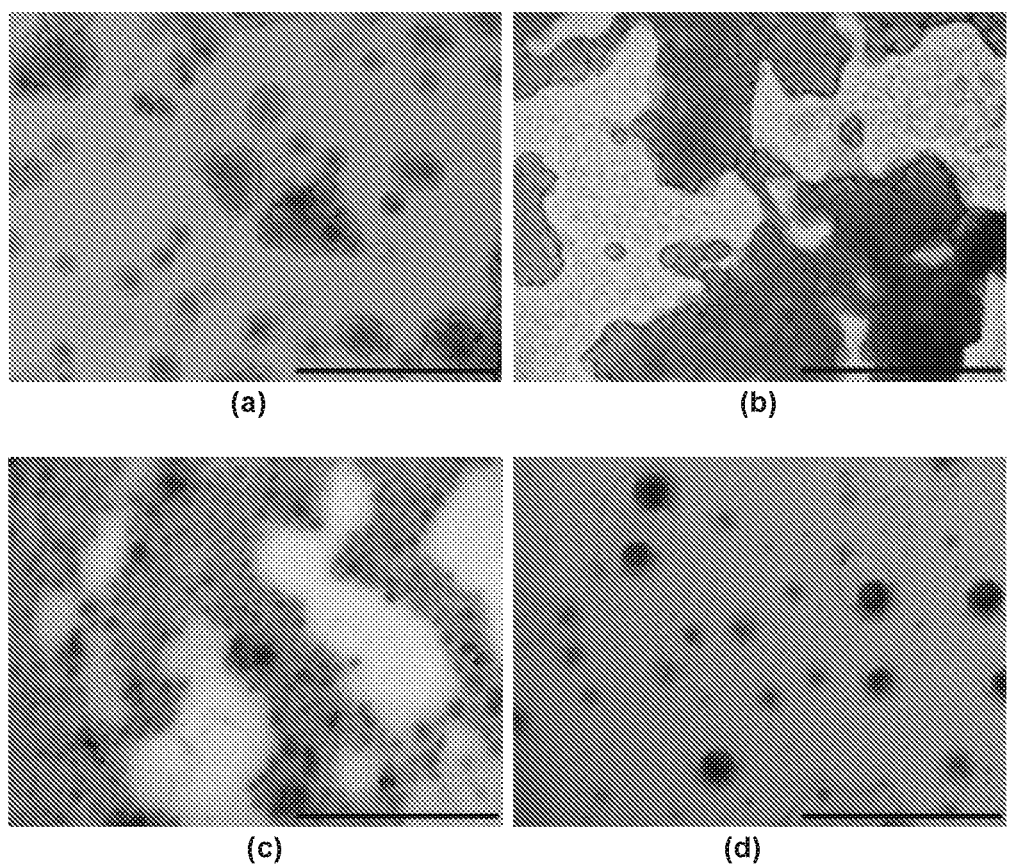
FIG. 5. Shows TEM images of (a) uncoated liposomes and (b) liposomes coated with L61 in water and (c) uncoated liposomes and (d) liposomes coated with L61 in methyl methacrylate (bar=1 µm)
Figure 6:
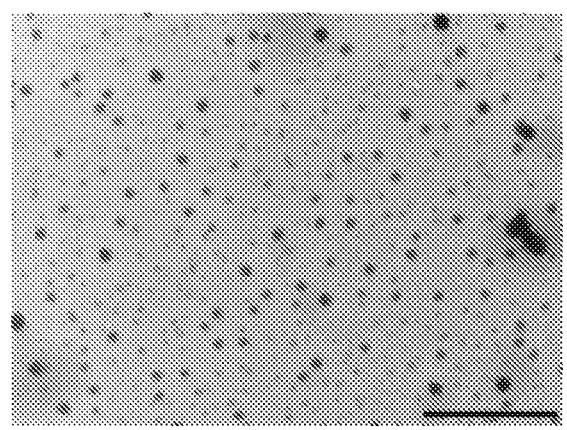
FIG. 6. Shows TEM image of liposomes coated with L61 in methyl methacrylate (bar=2 µm)

Although laser diffraction shows the effective diameter of Pluronic coated liposomes in methyl methacrylate to be roughly 400 nm, TEM images show the liposomes to in fact be closer to 100-120 nm in diameter and relatively well dispersed in methyl methacrylate when using Pluronics such as L61 (FIG. 5 and FIG. 6).

Table 3 shows examples of clinically approved liposomal-based therapeutics, with details of the liposome composition and the encapsulated drug. This table demonstrates the potential variety of stable lipid-drug combinations. Similarly, Table 4 shows the liposomal-based therapeutics currently undergoing clinical trials.

Formation of Stable Pluronic-Coated Liposome-Polymer Suspensions

Figure 7:
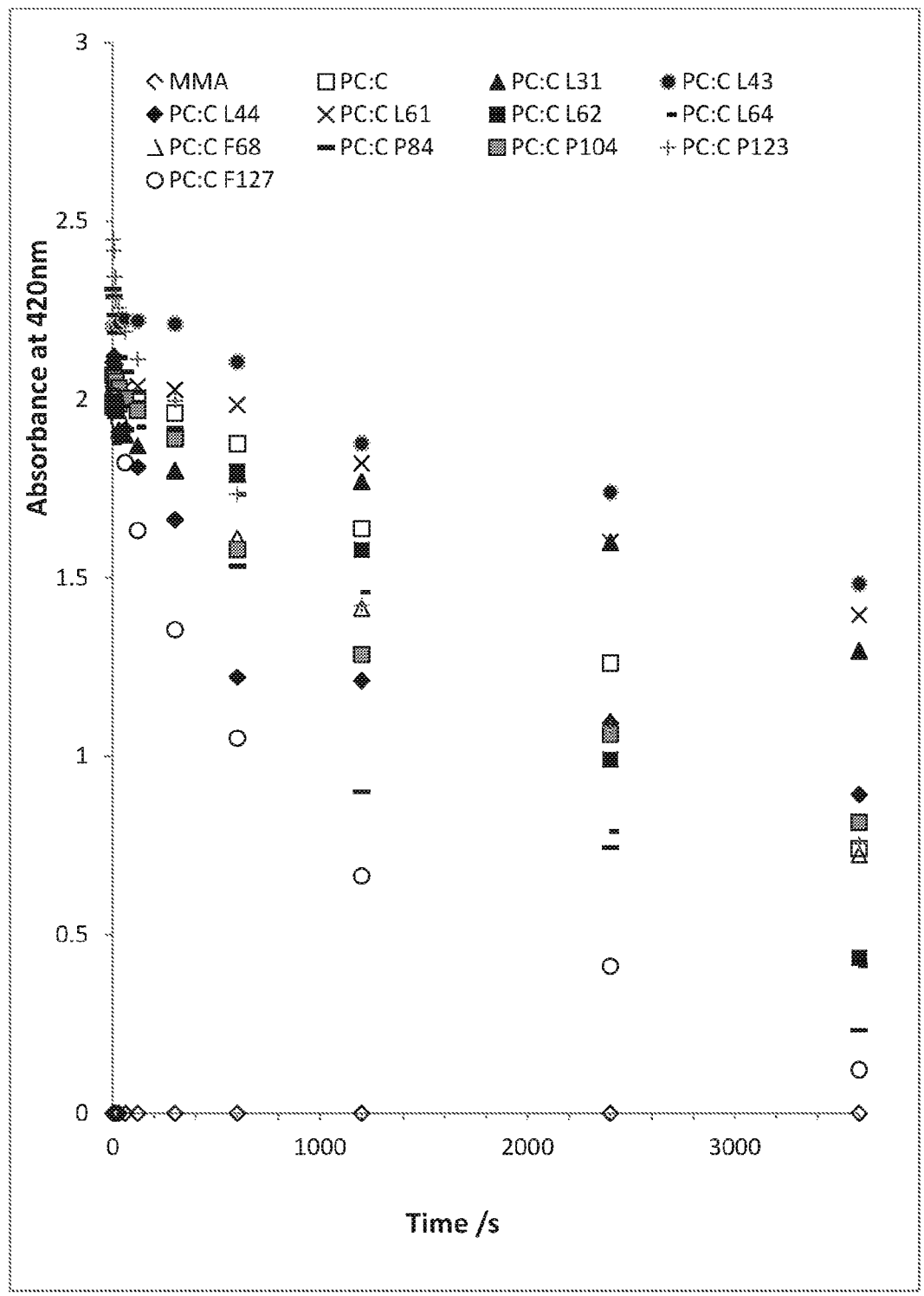
FIG. 7. Shows sedimentation rates of different Pluronic-coated liposomes in methyl methacrylate over time obtained by absorption measurements at 420 nm.

Absorbance values at 420 nm over time of the Pluronic coated liposomes in methyl methacrylate shows the three Pluronic-liposome combinations that achieved the smallest particle sizes (L31, L43 and L61) stay suspended in methyl methacrylate more effectively than all other liposome-Pluronic combinations tested (FIG. 7). It was clear when resuspending the liposome pellets that L31, L43 and L61 created stable suspensions in methyl methacrylate while the other Pluronic systems agglomerated and sedimented rapidly. L31, L43 and L61 coated liposomes could also be readily resuspended by agitation after extended periods of storage.

From this data it is apparent that L31, L43 and L61 Pluronics on the surface of 100 nm diameter liposomes create the most stable and well dispersed suspension of liposomes in methyl methacrylate. Analysis of the structure of these three Pluronics has found that all three Pluronics have an average molecular weight less than 2000 and a higher polypropylene oxide to polyethylene oxide ratio (see Table 2). Therefore Pluronics with an average $M_w \leq 2000$ and a higher polypropylene oxide to polyethylene oxide ratio form the most stable polymer suspensions.

Polymer-Coated Liposomal Cement Exhibits Superior Antibiotic Release

Figure 8:
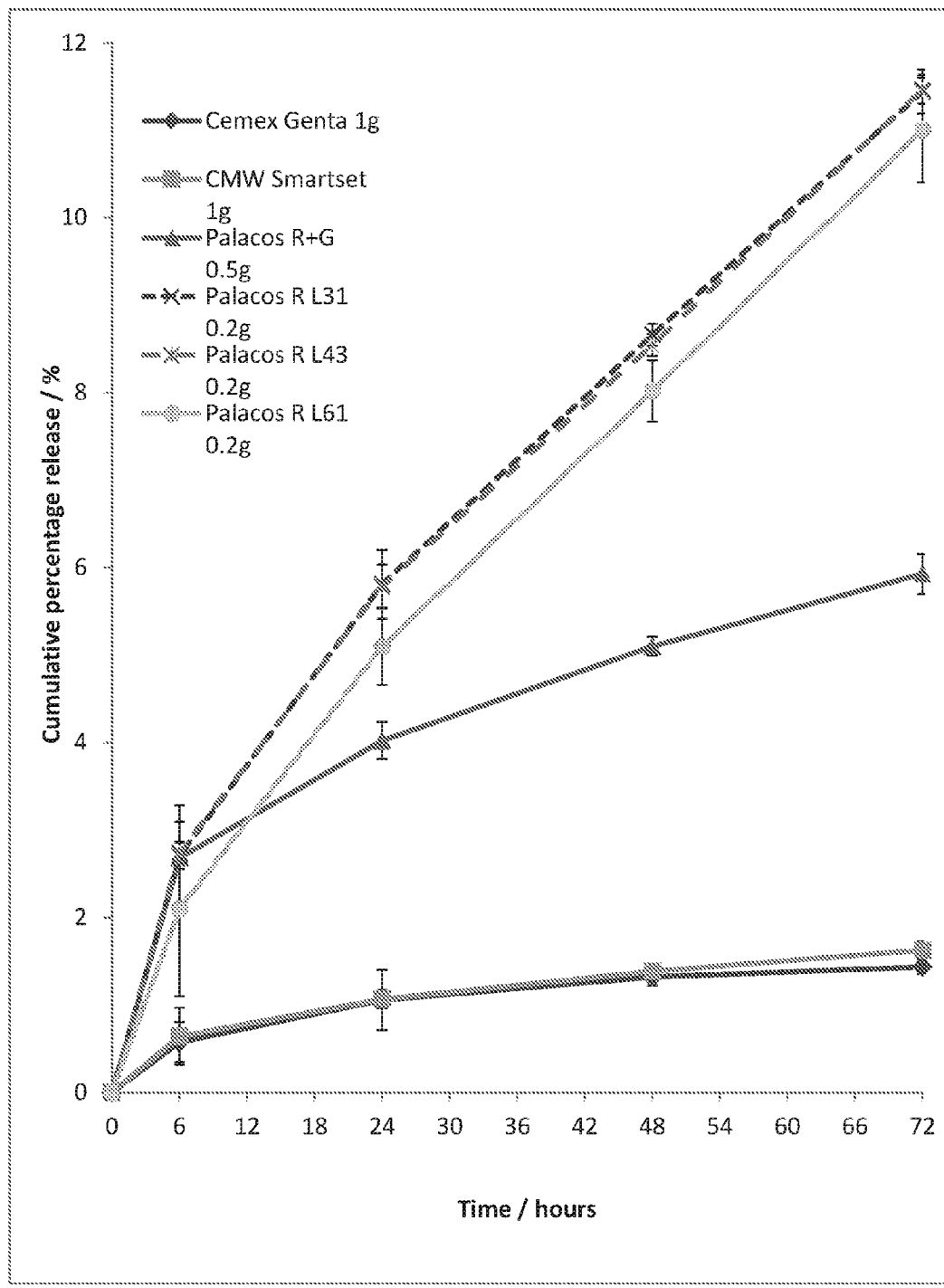
FIG. 8. Shows cumulative percentage gentamicin release after 72 hours from Cemex Genta, CMW smartest, Palacos R+G and Palacos R cement containing liposomes coated with Pluronics L31, L43 and L61 at the amount specified.
Figure 9:
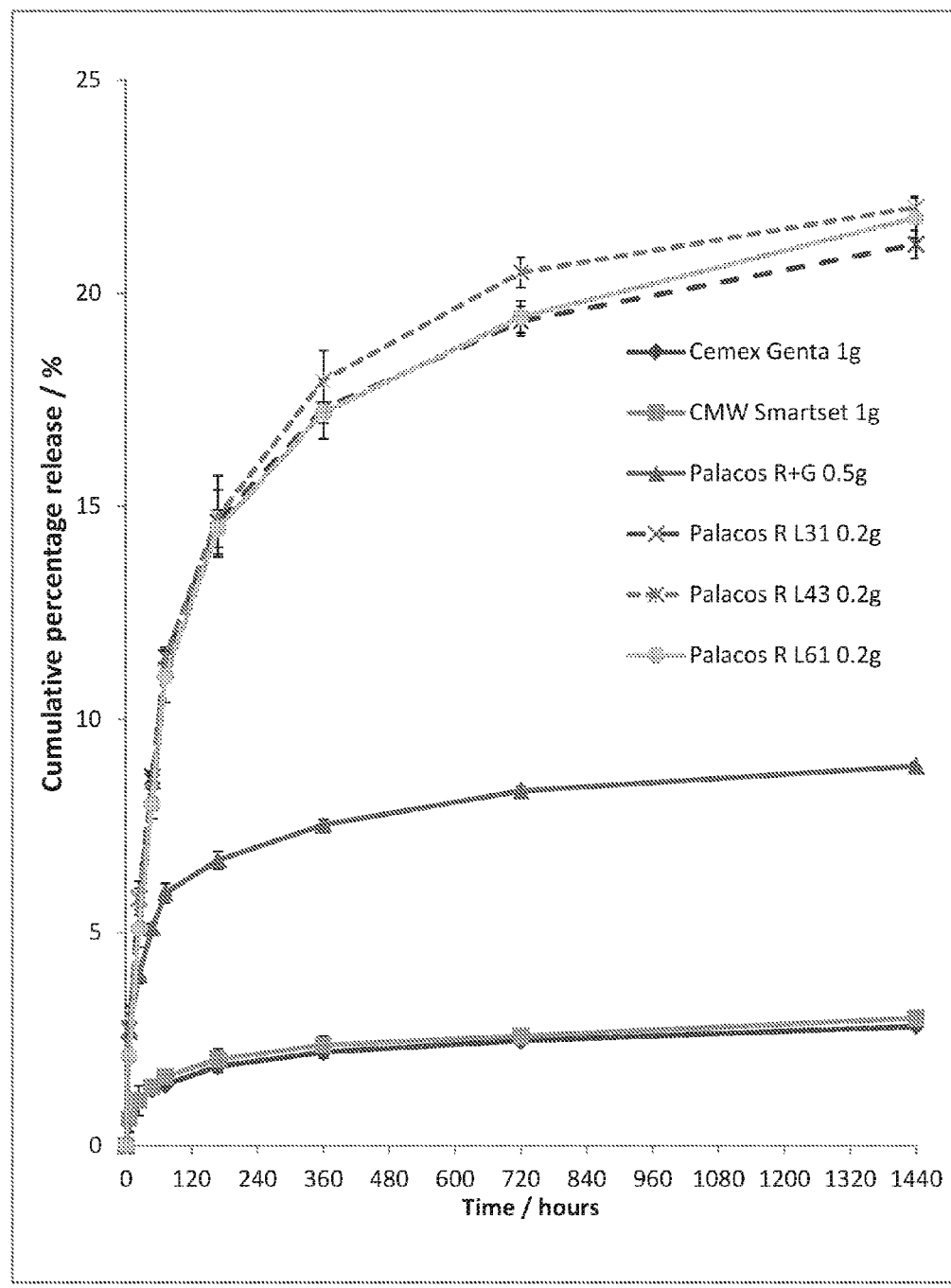
FIG. 9. Shows cumulative percentage gentamicin release after 1440 hours from Cemex Genta, CMW smartest, Palacos R+G and Palacos R cement containing liposomes coated with L31, L43 and L61 at the amount specified.

FIG. 8 shows the cumulative percentage release of the samples after 72 hours and FIG. 9 shows the cumulative percentage release of the samples over 1440 hours. The cumulative percentage release was calculated as the total amount of gentamicin detected by the assay at each time point as a percentage of the theoretical total amount of gentamicin in each sample. From the results it is clear that the liposomal system is much more efficient at releasing gentamicin than the current powdered antibiotic systems. The release is also sustained over the course of 1440 hours, whilst the powdered antibiotic bone cements experience a "dumping" effect which plateaus after 72 hours.

To demonstrate the antimicrobial efficacy of the liposomal system, coupons of Palacos R, Palacos R+G and the liposomal cement system with L61 Pluronic were placed on agar plates streaked with the bacteria S. aureus. The plates were incubated for 24 hours at 37° C. to allow the bacteria to grow. FIG. 10 shows the zones of inhibition obtained. The 10 ug gentamicin sulphate control created a zone of inhibition against S. aureus demonstrating the bacteria is susceptible to gentamicin. There was no antibacterial activity for Palacos R. Sample 1 of Palacos R+G gave the largest zone of inhibition; however sample 2 and 3 demonstrates how inconsistent the zones were due to poor antibiotic dispersion on the surface of the sample, regardless of the high levels of gentamicin sulphate present. Palacos R L61 created consistent zones of inhibition, highlighting that not only is the gentamicin sulphate well dispersed but also that the encapsulated gentamicin sulphate is readily accessible to inhibit bacterial growth.

Pluronic-Coated Liposomal Cement Exhibits Reduced Porosity

Figure 11A:
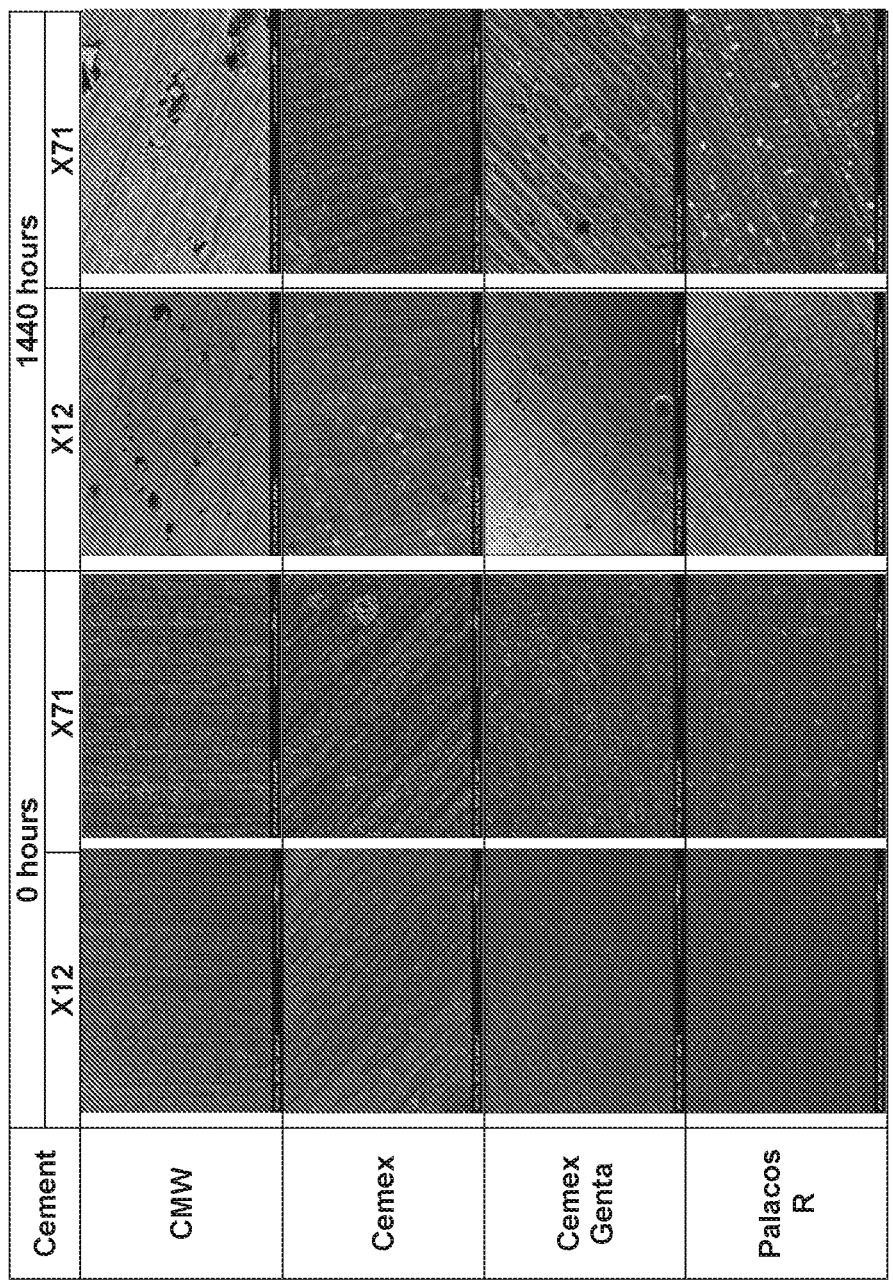
FIG. 11a. Shows SEM images of CMW smartest, Cemex, Cemex Genta, Palacos R before and after 1440 hours in Ringer's solution.
Figure 11B:
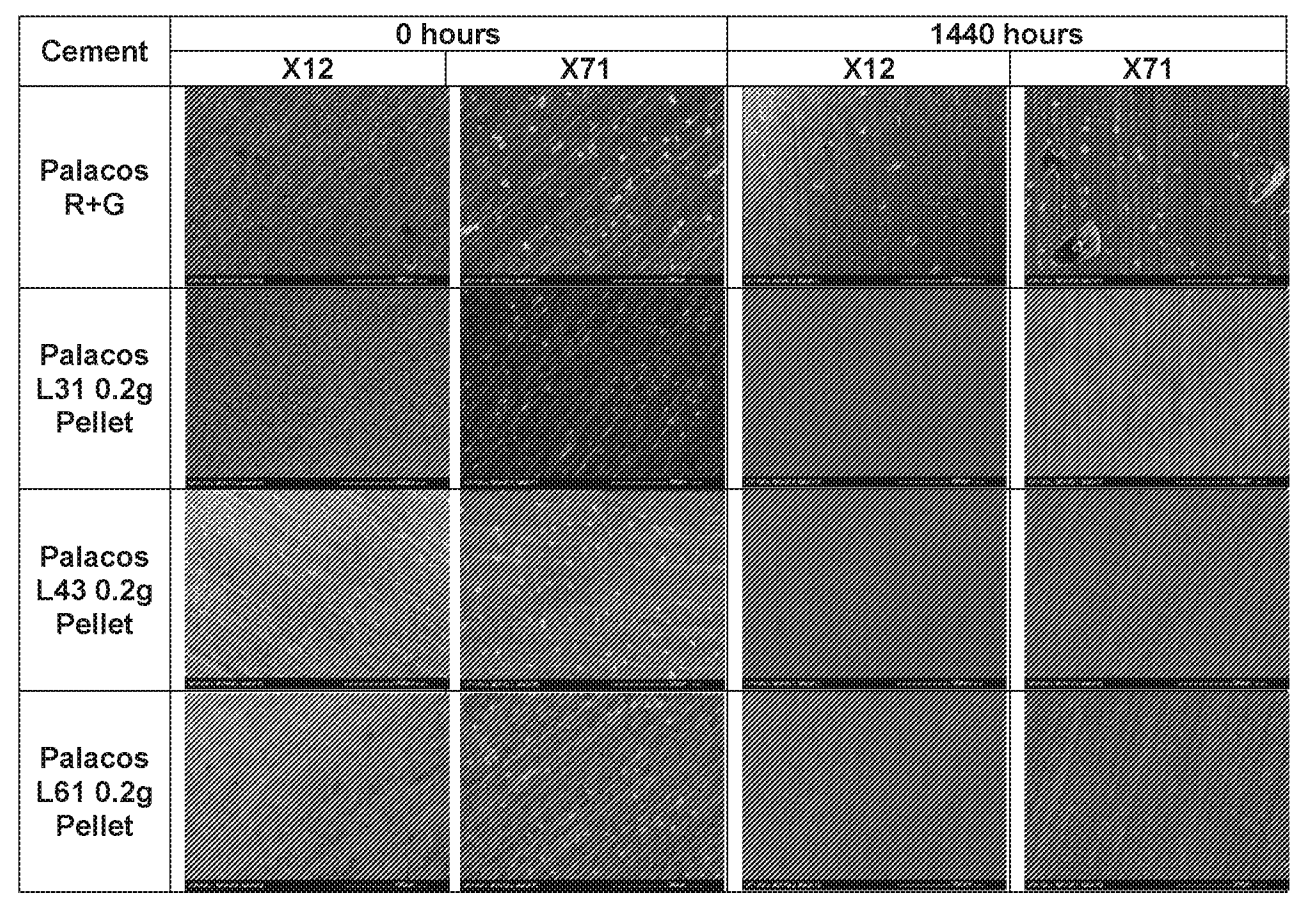

FIG. 11 shows SEM images taken of the samples prior to storage in Ringer's solution and after storage in Ringer's solution for 1440 hours. All commercial cements which used powdered antibiotics resulted in large pores appearing after the antibiotic was released whilst cements without antibiotics and the liposomal bone cements demonstrated no substantive porosity after 1440 hours in Ringer's solution. Closer inspection of the surface of liposomal bone cements after 1440 hours shows barely visible sub-micron sized pores where the liposomes were released.

Figure 12:
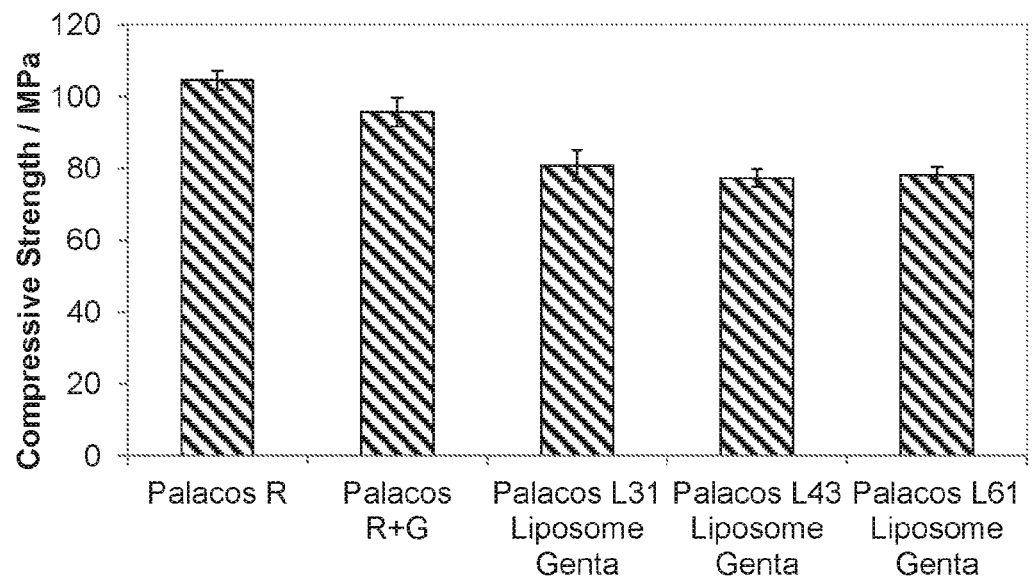
FIG. 12. Shows compressive strength of commercial Palacos R and Palacos R+G cements, with and without antibiotic respectively, when compared with Palacos R containing liposomes coated with Pluronics L31, L43 and L61.

Pluronic-Coated Liposomal Cement Shows Acceptable Compressive and Improved Bending Strength and Fracture Toughness FIG. 12 shows the compressive strength of Palacos R, Palacos R+G and the liposomal antibiotic bone cement using L31, L43 or L61 Pluronics. Although a reduction was observed for the liposomal system, the compressive strength of the cement remained above the ISO5833 minimum requirement (70 MPa).

Figure 13:
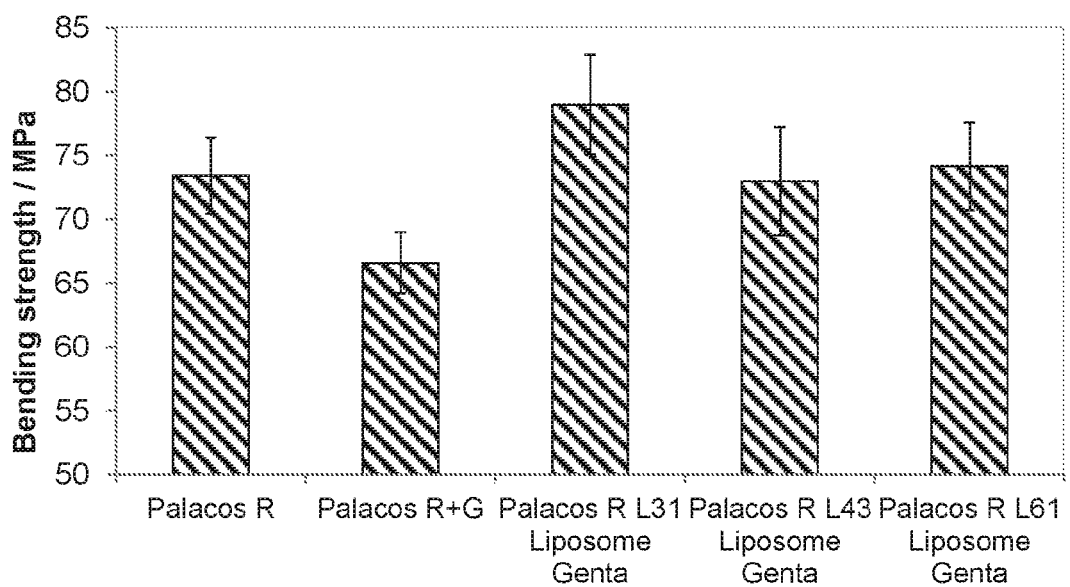
FIG. 13. Shows bending strength of commercial Palacos R and Palacos R+G cements, with and without antibiotic respectively, when compared with Palacos R containing liposomes coated with Pluronics L31, L43 and L61.
Figure 14:
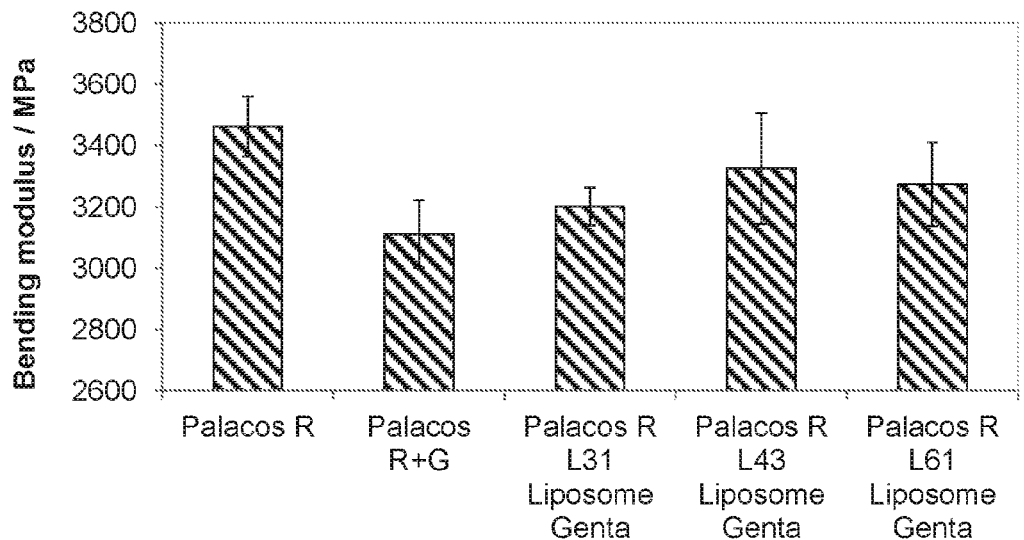
FIG. 14. Shows bending modulus of commercial Palacos R and Palacos R+G cements, with and without antibiotic respectively, when compared with Palacos R containing liposomes coated with Pluronics L31, L43 and L61.

FIG. 13 shows the bending strength of Palacos R, Palacos R+G and the liposomal antibiotic bone cement using L31, L43 and L61 Pluronics. Overall the liposomal system had significantly better (ANOVA, $P \leq 0.05$) bending strength than the commercially available powdered gentamicin system (Palacos R+G), but not significantly different when compared to Palacos R. Palacos R was found to have significantly higher bending modulus than Palacos R+G (FIG. 14). There were no significant differences when comparing the liposomal antibiotic cements with Palacos R and Palacos R+G.

Figure 15:
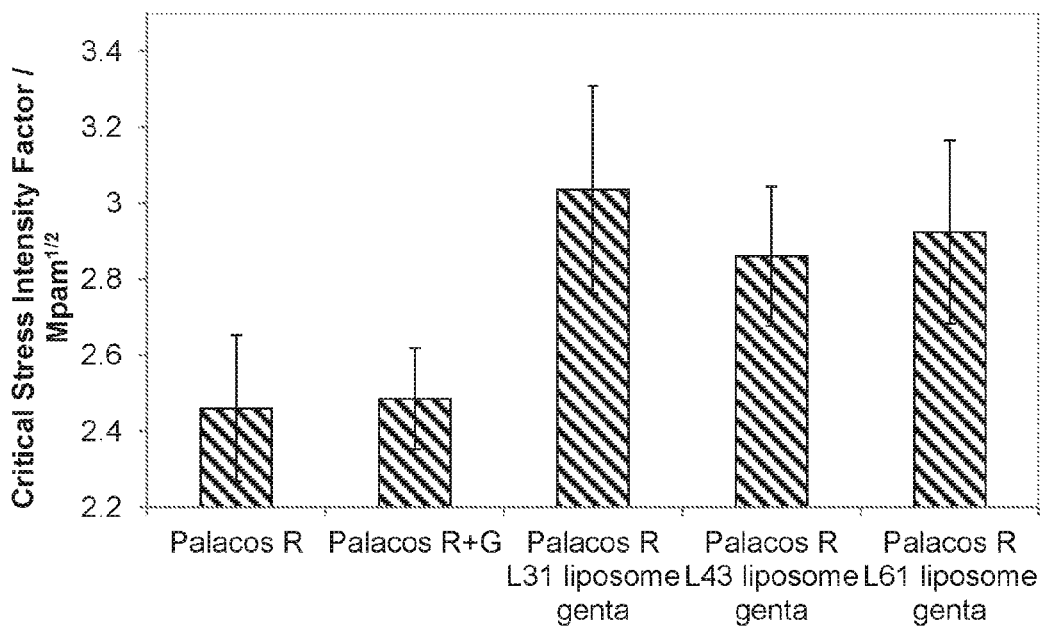
FIG. 15. Shows fracture toughness of commercial Palacos R and Palacos R+G cements, with and without antibiotic respectively, when compared with with Palacos R containing liposomes coated with Pluronics L31, L43 and L61.
Figure 16:
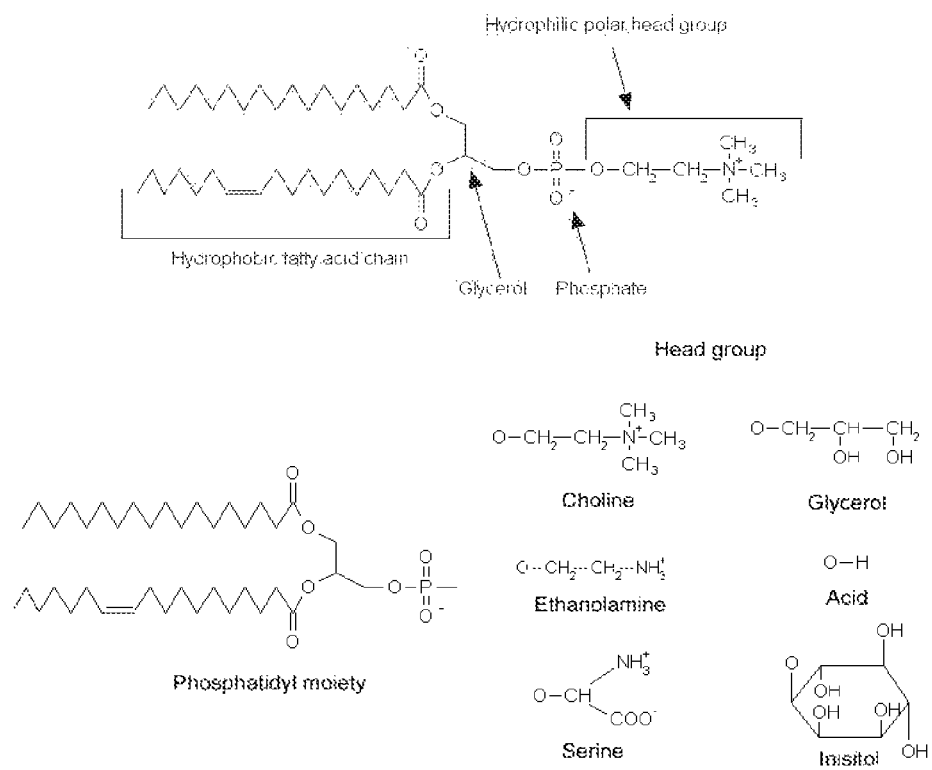
FIG. 16. Shows the structure of a typical phospholipid. This consists of two hydrophobic fatty acid chains connected by a glycerol molecule and a phosphate molecule to an hydrophilic head group. The presence of both hydrophobic and hydrophilic parts result in an amphiphatic molecule. Phospholipids form the bilayer of liposomes, with a layer of lipids orientated with the hydrophilic head groups facing outwards and a layer of the lipids with the hydrophilic head groups orientated inwards (FIG. 2). The different head groups of naturally-occurring phospholipids are also shown. Phospatidylcholine and phosphatidylethanolamine are neutral as the positive charge of the head group and the negative charge of the phosphate molecule neutralise one another. These lipids are also referred to as zwitterionic, i.e. they comprise both positive and negative charged groups. Sphingomyelin containing liposomes are also considered neutral. Phospholipids with a neutral head group are negatively charged due to the negative charge of the phosphate molecule. Negatively charged liposomes are those which contain phosphatidic acid, glycerol, serine and inositol head groups. Certain lipids exist which do not have phosphatidyl moieties. The charge on these lipids is governed mainly by the charge on the hydrophilic head group. This has allowed for the manufacture of synthetic cationic (positively charged) liposomes. Examples of cationic liposomes include DOTAP, DODAc, DMRIE, DOSPA, DMTAP, DSTAP, DODAP, DOBAQ, DDAB and DOGS.

FIG. 15 shows the fracture toughness (critical stress intensity factor) of Palacos R, Palacos R+G and the liposomal antibiotic bone cement using L31, L43 or L61 Pluronics. All liposomal cements had significantly better fracture toughness over Palacos R and Palacos R+G. The increased fracture toughness may be attributed to the well dispersed 100 nm liposomes, inducing toughening mechanisms in the cement perhaps similar to rubber particles.

SUMMARY

We show that the encapsulation of antibiotics within Pluronic-coated liposomal vesicles results in a well dispersed suspension. This system is stable throughout a range of temperatures (4-80° C.) and has been shown to survive the exothermic process of setting bone cement. When this liposomal suspension is incorporated into the liquid component of the bone cement and thus the polymer matrix, a better overall dispersion of the antibiotic is observed compared to conventional techniques which tend to agglomerate antibiotic powder particles, thereby preventing uniform and controlled release of the antibiotic from the bulk of the cement. Therefore this invention improves the dispersion of the antibiotic within the bone cement matrix and, as a result of this, improves the release characteristics. Moreover, advantageously it has been found that by adsorbing amphiphilic block copolymers (Pluronics) on the surface of the liposomes and incorporating these into cements, then those cements including the same exhibit enhanced structural and mechanical properties.

REFERENCES

1. Davis E J R, International A. Handbook of Materials for Medical Devices: ASM International; 2003.
2. Sampath S S, Robinson D H. Comparison of new and existing spectrophotometric methods for the analysis of tobramycin and other aminoglycosides. J Pharm Sci. 1990; 79(5):428-431.
3. Zhang X, Wyss U P, Pichora D, Goosen M F A. Biodegradable Controlled Antibiotic Release Devices for Osteomyelitis: Optimization of Release Properties. J Pharm Pharmacol, 1994; 46(9):718-724.
4. Institution BS. ISO5833:2002 Implants for surgery: Acrylic resin cements. BSI, London. 2002.
5. Institution BS. ISO13586:2000 Plastics: Determination of fracture toughness (Gic and Kic). Linear elastic fracture mechanics (LEFM) approach. BSI, London. 2000.

TABLE 1

Particle diameters of Pluronic-coated PC:C liposomes in methyl methacrylate measured by laser diffraction

| | Size/nm |
|---|---|
| PC:C | 870 ± 400 |
| L31 | 380 ± 180 |
| L43 | 390 ± 150 |
| L44 | 1580 ± 120 |
| L61 | 450 ± 200 |

TABLE 1-continued

Particle diameters of Pluronic-coated PC:C liposomes in methyl methacrylate measured by laser diffraction

|  | Size/nm |
|---|---|
| L62 | 2020 ± 860 |
| L64 | 1080 ± 520 |
| F68 | 1100 ± 490 |
| P84 | 840 ± 370 |
| P104 | 920 ± 440 |
| P123 | 750 ± 250 |
| F127 | 6160 ± 2860 |

TABLE 2

Pluronics and their properties (tested Pluronics underlined):

| State | Pluronic Number | Cloud point | Pour point | Mw of PPO | % PEO Content | Mw of PEO | Average Mw | No of PPO Chains | No of PEO Chains | HLB | HLB Group | HLB Description | Calculated HLB | BASF HLB |
|---|---|---|---|---|---|---|---|---|---|---|---|---|---|---|
| L | 10 | 32 | −5 | 300 | 0 | 0 | 3200 | 5 | 0 | 14 | 13 to 15 | Detergents-O/W emulsifier | 6 | 12 to 18 |
| L | 31 | 37 | −32 | 900 | 10 | 110 | 1100 | 15 | 2 | 4.5 | 3 to 6 | W/O emulsifier | 5 | 1 to 7 |
| L | 35 | 73 | 7 | 900 | 50 | 950 | 1900 | 15 | 21 | 18.5 | N/A | N/A | N/A | 18 to 23 |
| F | 38 | >100 | 48 | 900 | 80 | 3760 | 4700 | 15 | 85 | >24 | N/A | N/A | N/A | >24 |
| L | 43 | 42 | −1 | 1200 | 30 | 555 | 1850 | 21 | 12 | 12 | 8 to 12 | O/W emulsifier | 7 | 7 to 12 |
| L | 44 | 65 | 16 | 1200 | 40 | 880 | 2200 | 21 | 20 | 16 | 15 to 18 | Solubilizing agent | N/A | 12 to 18 |
| L | 61 | 17 | −30 | 1800 | 10 | 200 | 2000 | 31 | 4 | 3 | 3 to 6 | W/O emulsifier | 4 | 1 to 7 |
| L | 62 | 35 | −1 | 1800 | 20 | 472 | 2360 | 31 | 10 | 7 | 7 to 9 | Wetting agent | 5 | 1 to 7 |
| L | 64 | 58 | 16 | 1800 | 40 | 1160 | 2900 | 31 | 26 | 15 | 13 to 15 | Detergents-O/W emulsifier | N/A | 12 to 18 |
| P | 65 | 82 | 27 | 1800 | 50 | 1700 | 3400 | 31 | 38 | 17 | 15 to 18 | Solubilizing agent | N/A | 12 to 18 |
| F | 68 | >100 | 52 | 1800 | 80 | 6720 | 8400 | 31 | 152 | 29 | N/A | N/A | N/A | >24 |
| F | 77 | >100 | 48 | 2100 | 70 | 4620 | 6600 | 36 | 104 | >24 | N/A | N/A | N/A | >24 |
| L | 81 | 20 | −37 | 2400 | 10 | 275 | 2750 | 41 | 6 | 2 | N/A | N/A | 3 | 1 to 7 |
| P | 84 | 74 | 34 | 3200 | 40 | 1680 | 4200 | 55 | 38 | 14 | 13 to 15 | Detergents-O/W emulsifier | N/A | 12 to 18 |
| P | 85 | 85 | 34 | 3200 | 50 | 2300 | 4600 | 55 | 52 | 24 | N/A | N/A | N/A | 12 to 18 |
| F | 87 | >100 | 49 | 3200 | 70 | 5390 | 7700 | 55 | 122 | 24 | N/A | N/A | N/A | >24 |
| F | 88 | >100 | 54 | 3200 | 80 | 9120 | 11400 | 55 | 207 | 28 | N/A | N/A | N/A | >24 |
| L | 92 | 26 | 7 | 2700 | 20 | 730 | 3650 | 46 | 16 | 5.5 | 3 to 6 | W/O emulsifier | 4 | 1 to 7 |
| F | 98 | >100 | 58 | 2700 | 80 | 10400 | 13000 | 46 | 236 | >24 | N/A | N/A | N/A | >24 |
| L | 101 | 15 | −23 | 3000 | 10 | 380 | 3800 | 52 | 8 | 1 | N/A | N/A | 2 | 1 to 7 |
| P | 103 | 86 | 30 | 3000 | 30 | 1485 | 4950 | 52 | 33 | 7 to 12 | 8 to 12 | O/W emulsifier | N/A | 7 to 12 |
| P | 104 | 81 | 32 | 3000 | 40 | 2360 | 5900 | 52 | 53 | 12 to 18 | 15 to 18 | Solubilizing agent | N/A | 12 to 18 |
| P | 105 | 91 | 35 | 3000 | 50 | 3250 | 6500 | 52 | 73 | 12 to 18 | 15 to 18 | Solubilizing agent | N/A | 12 to 18 |
| F | 108 | >100 | 57 | 3000 | 80 | 11680 | 14600 | 52 | 265 | >24 | N/A | N/A | N/A | >24 |
| L | 121 | 14 | 5 | 3600 | 10 | 440 | 4400 | 62 | 10 | 0.5 | N/A | N/A | 1 | 1 to 7 |
| P | 123 | 90 | 31 | 3600 | 30 | 1725 | 5750 | 62 | 39 | 7 to 12 | 8 to 12 | O/W emulsifier | N/A | 7 to 12 |
| F | 127 | >100 | 56 | 3600 | 70 | 8820 | 12600 | 62 | 200 | 22 | N/A | N/A | N/A | 18 to 23 |

TABLE 3

Clinically approved liposomal-based therapeutics

| Trade name | Company | Liposome composition | Liposome charge | Drug | Drug type | Form/storage time | Indications |
|---|---|---|---|---|---|---|---|
| Abelcet | Enzon, Cephalon | DMPC and DMPG (7:3 molar ratio) | Negative | Amphoterecin B | Polyene antimycotics | Suspension/24 months | Fungal infections |
| AmBisome | Gilead Sciences, NeXstar | HSPC, DSPG and cholesterol (2:0.8:1 molar ratio) | Negative | Amphoterecin B | Polyene antimycotics | Powder/36 months | Fungal and protozoal infections |
| Amphotec | Sequus | Cholesteryl sulfate | Negative | Amphotericin B | Polyene antimycotics | Powder/24 months | Fungal infections |

TABLE 3-continued

Clinically approved liposomal-based therapeutics

| Trade name | Company | Liposome composition | Liposome charge | Drug | Drug type | Form/storage time | Indications |
|---|---|---|---|---|---|---|---|
| DepoCyt | SkyePharma, Napp | DOPC, DPPG, Cholesterol and Triolein (7:1:11:1 molar ratio) | Negative | Cytarabine | Antineoplastics | Suspension/18 months | Malignant lymphomatous meningitis |
| DaunoXome | Gilead Sciences, NeXstar, Galen | DSPC and cholesterol (2:1 molar ratio) | Neutral | Daunorubicin citrate | Antineoplastics | Emulsion/12 months | HIV-related Kaposi's sarcoma |
| Myocet | Zeneus, Cephalon | EPC and cholesterol (55:45 molar ratio) | Neutral | Doxorubicin hydrochloride | Antineoplastics | Powder/18 months | Combination therapy with cyclophosphamide in metastatic breast cancer |
| Epaxal | Berna Biotech, Janssen-Cilag | DOPC and DOPE | Neutral | Inactivated hepatitis A virus (haemagglutinin) | Vaccine | Suspension/36 months | Hepatitis A |
| Inflexal V | Berna Biotech, Janssen-Cilag | DOPC and DOPE | Neutral | Influenza virus surface antigens (haemagglutinin and neuraminidase) | Vaccine | Suspension/12 months | Influenza |
| DepoDur | SkyePharma, Endo | DOPC, DPPG, cholesterol, Triolein (7:1:11:1 molar ratio) | Negative | Morphine sulphate pentahydrate | Analgesic | Suspension/24 months | Postsurgical analgesia |
| Visudyne | QLT, Novartis | EPG and DMPC (3:5 molar ratio) | Neutral | Verteporfin | Photosensitizing agent | Powder/48 months | Age-related macular degeneration, pathologic myopia, ocular histoplasmis |
| Doxil/Caelyx | Ortho Biotech, Schering-Plough, Seqqus, Janssen-Cilag | HSPC, cholesterol and PEG 200-DSPE (56:39:5 molar ratio) | Neutral | Doxorubicin hydrochloride | Antineoplastics | Suspension/20 months | HIV-related Kaposi's sarcoma, metastatic breast cancer, metastatic ovarian cancer and prostate cancer |
| Estrasorb | Novavax | HSPC | Neutral | Estradiol hemihydrate | Hormone | Emulsion/36 months | Menopausal therapy |

TABLE 4

Liposome-based therapeutics in clinical trials

| Trade name | Company | Liposome composition | Liposome charge | Drug | Drug type | Indication |
|---|---|---|---|---|---|---|
| LEP-ETU | NeoPharm | DOPC, cholesterol and cariolipin (90:5:5 molar ratio) | Negative | Paclitaxel | Mitotic inhibitor | Ovarian, breast, lung cancer |
| LEM-ETU | NeoPharm | DOPC, cholesterol and cariolipin (90:5:5 molar ratio) | Negative | Mitoxantrone | Antineoplastics | Leukemia, breast, stomach, liver, ovarian cancers |
| EndoTAG-1 | Medigene | DOTAP, DOPC and paclitaxel (50:43:3 molar ratio) | Positive | Paclitaxel | Mitotic inhibitor | Anti-angiogenic properties, breast cancer, pancreatic cancer |
| Arikace | Insmed | DPPC and cholesterol | Neutral | Amikacin | Aminoglycoside antibiotic | Lung infection |
| Marqibo | Talon therapeutics | Egg sphingomyelin and cholesterol (55:45 molar ratio) | Negative | Vincristine | Mitotic inhibitor | Metastatic malignant uveal melanoma |
| ThermoDox | Celsion | DPPC, MSPC and PEG 200-DSPE (90:10:4 molar ratio) | Neutral | Doxorubicin hydrochloride | Antineoplastics | Non-resectable hepatocellular carcinoma |
| Atragen | Aronex | DMPC and soybean oil | Neutral | Tretinoin | Antineoplastics | Acute promyelocytic leukemia hormone-refractory prostate cancer |

TABLE 4-continued

Liposome-based therapeutics in clinical trials

| Trade name | Company | Liposome composition | Liposome charge | Drug | Drug type | Indication |
|---|---|---|---|---|---|---|
| T4N5 liposome lotion | AGI Dermatics | Unknown | — | Bacteriphage T4 endonuclease 5 | Bacteriphage/Enzyme | Xeroderma pigmentosum |
| Liposomal Grb-2 | Bio-Path | Unknown | — | Grb2 antisense, oligodeoxynucelotide | Synthetic DNA | Acute myeloid leukemia, chronic myelogenous leukemia, acute lymphoblastic leukemia |
| Nyotran | Aronex | DMPC, DMPG and cholesterol | Negative | Nystatin | Polyene antimycotics | Systemic fungal infections |
| LE-SN38 | NeoPharm, IInsys Therapeutics | DOPC, cholesterol and cardiolipin | Negative | SN-38 | Metabolite | Metastatic colorectal cancer |
| Aroplatin | Antigenics | DMPC and DMPG | Negative | Cisplatin | Antineoplastics | Metastatic colorectal cancer |
| Liprostin | Endovasc | Unknown | — | Prostaglandin E1 | Antiulcerative | Peripheral vascular disease |
| Stimuvax | Merck KGaA | Monophosphoryl lipid A, cholesterol, DMPG and DPPC | Negative | BLP25 lipopeptide | Vaccine | Cancer vaccine for multiple myeloma developed encephalitis |
| SPI-077 | Sequus | SHPC, cholesterol, DSPE-PEG | Neutral | Cisplatin | Antineoplastics | Head and neck cancer, lung cancer |
| Lipoplatin | Regulon | SPC, DPPG, cholesterol and mPEG 2000-DSPE | Negative | Cisplatin | Antineoplastics | Pancreatic cancer, head and neck cancer, mesothelioma, breast and gastric cancer, non-squamous non-small-cell lung cancer |
| S-CKD602 | Alza | DPSC and DSPE-PEG (95:5 molar ratio) | Neutral | Camptothecin | Drug intermediate | Recurrent and progressive carcinoma of the uterine cervix |
| OSI-211 | OSI Pharmaceuticals | HSPC, cholerstol (2:1 molar ratio) | Neutral | Lurtotecan | Anti-histamine | Ovarian cancer, head and neck cancer |
| INX-0125 | Inex | Egg sphingomyelin and cholesterol (55:45 molar ratio) | Neutral | Vinorelbine | Mitotic inhibitor | Advanced solid tumors |
| INX-0076 | Inex | Egg sphingmyelin and cholesterol (55:45 molar ratio) | Neutral | Topoitecan | Antineoplastics | Advanced solid tumors |
| Liposome-Annamycin | Callisto | DSPC and DSPG | Negative | Annamycin | Anthracycline antibiotic | Acute lymphocytic leukemia |
| SLIT Cisplatin | Transave | DPPC and cholesterol | Neutral | Cisplatin | Antineoplastics | Cancer treatments |
| AeroLEF | Delex Therapeutics | EPC/SPC, cholesterol | Neutral | Fentanyl | Analgesic | Pain treatment |
| Onco TCS | Inex, Enzon | DSPC, cholesterol | Neutral | Vincristine sulfate | Antineoplastic Agents | Cancer treatments |
| Allovectin-7 | Vical | DMRIE and DOPE | Positive | HLA-B7 plasmid | Gene | Gene therapy of metastatic cancers |
| Annamycin | Aronex | DMPC, DPPC, DMPG, Sterylamine (SA), cholesterol | Negative | Annamycin | Anthracycline antibiotic | Breast cancer |

The invention claimed is:

1. A bone cement having dispersed therein a vehicle for delivering and dispersing at least one antibiotic in said bone cement, wherein said vehicle comprises a liposome containing said at least one antibiotic, further wherein said liposome also comprises a block co-polymer adsorbed or absorbed onto the liposome, the block co-polymer having an average molecular weight less than 2000 and a higher proportion of polypropylene oxide to polyethylene oxide.

2. The bone cement according to claim 1 wherein said liposome is selected from the group comprising: a liposome less than 600 nm in diameter when measured using laser diffraction; a liposome less than 150 nm in diameter when measured using Transmission Electron Microscopy (TEM); and a liposome about 100 nm in diameter using TEM.

3. The bone cement according to claim 1 wherein said liposome is made from a phospholipid selected from the group consisting of: cationic phospholipids, neutral phospholipids, anionic phospholipids and one or more combinations thereof.

4. The bone cement according to claim 1 wherein said liposome is made from at least one phospholipid selected from the following groups: phospatidylcholine, phosphatidylethanolamine, sphingomyelin, phosphatidic acid, phospatidylglycerol, phospatidylserine and phospatidylinositol.

5. The bone cement according to claim 1 wherein said liposome is made from at least one cationic lipid selected from the following groups: 1,2 dioleoyl-3-trimethylammonium-propane (DOTAP), dioctadecyldimethylammonium chloride (DODAc), 1,2-dimyristoyloxypropyl-3-dimethylhydroxyethyl ammonium (DMRIE), 2,3-dioleoyloxy-N-(2 (sperminecarboxamide)ethyl)-N,N-dimethyl-1 propananninium (DOSPA), 1,2-dimethyldioctadecylammoniumbromide (DDAB), 2-dioleyl-3-N,N,N-trimethylaminopropanechloride (DOTMA), 1,2-dimyristoyl-3-trimethylammoniumpropane DMTAP, 1,2-distearoyl-3-trimethylammoniumpropane (DSTAP), 1,2-Dioleoyl-3-dimethylammonium-propane (DODAP), 1,2-dioleoyl-sn-glycero-3-phosphoethanolamine, N-(4-carboxybenzyl)-N,N-dimethyl-2,3-bis(oleoyloxy)propan-1-aminium (DOBAQ) and dioctadecylamidoglycylspermine (DOGS).

6. The bone cement according to claim 1 wherein said liposome is selected from the group consisting of: dimyristoyl-phosphatidylcholine (DMPC), dimyristoylphosphatidylglycerol (DMPG), hydrogenated soy phosphatidylcholine (HSPC), distearoylphosphatidylglycerol-cholesterol (DSPG), cholesteryl sulfate, 1,2-dioleoyl-sn-glycero-3-phosphatidylcholine (DOPC), 1.2-dipalmitoyl-sn-3-glycero-[phosphorrac-(1-glycerol)] (DPPG), 1,2-distearoyl-sn-glycero-3-phosphocholine (DSPC), egg yolk phosphatidylcoline (EPC), Dioleoylphosphatidylethanolamine, egg phosphatidylglycerol (ePG), Polyethylene glycol (PEG)-dendron phospholipids, Dipalmitoylphosphatidylcholine (DPPC), 1,2-distearoyl-sn-glycero-3-phosphoethanolamine-N-[methoxy(polyethyleneglycol)-2000] (PEG200 DSPE), monostearoylphosphatidylcholine (MSPC), 1-stearoyl-L-α-phosphatidyl (SHPC), Soybean phospholipids (SPC), egg sphingomyelin, stearylamine (SA), and 1,2-dimyristyloxypropyl-3-dimethyl-hydroxyl ethyl ammonium bromide (DMRIE).

7. The bone cement according to claim 1 wherein said block co-polymer is selected from the group consisting of: Pluronic L31, Pluronic L43 and Pluronic L61.

8. The bone cement according to claim 1 wherein said antibiotic is selected from the list consisting of: gentamicin, vancomycin, tobramycin, ampicillin, benzylpenicillin, erythromycin, kanamycin, methicillin, neomycin, streptomycin, tetracycline, co-trimoxazole, cloxacillin, chloramphenicol, cephaloridine, cephazolin, oxacillin, ciprofloxacin, aztreonam and imipenem.

9. The bone cement according to claim 1 wherein said antibiotic comprises two or more antibiotics.

10. The bone cement according to claim 1 wherein said cement is selected from the group consisting of: poly(methyl methacrylate) (PMMA), methacrylate-cements and acrylic resins.

11. The bone cement according to claim 1 wherein said cement comprises a plurality of said liposomes.

12. The bone cement according to claim 11 wherein said plurality of liposomes is selected from one or more of the groups consisting of: liposomes made from the same lipid; liposomes made from the same two or more different lipids; different liposomes made from a different lipid; different liposomes made from two or more different lipids; liposomes made from the same one or more lipid(s) but containing different antibiotics; and liposomes made from different one or more lipids but containing different antibiotics.

13. The bone cement according to claim 1 wherein said vehicle or said cement also comprises an agent selected from the group consisting of: other antimicrobial agents, drugs to stimulate bone formation, therapeutic agents, strontium, bisphosphonates and bone morphogenetic proteins.

14. A method for the manufacture of bone cement comprising mixing together a polymer suitable for making bone cement, or a precursor thereof, with a vehicle for delivering and dispersing at least one antibiotic within said bone cement; wherein said vehicle comprises a liposome containing said antibiotic; and further wherein said liposome comprises a block co-polymer adsorbed or absorbed onto the liposome, the block co-polymer having an average molecular weight less than 2000 and a higher proportion of polypropylene oxide to polyethylene oxide.

15. The method according to claim 14 wherein said precursor is a monomer.

16. The method according to claim 14 wherein a suspension of said vehicle is mixed into a liquid component of the bone cement prior to mixing this liquid component with the polymer or precursor thereof.

\* \* \* \* \*